(12) United States Patent
Ni et al.

(10) Patent No.: US 7,731,966 B2
(45) Date of Patent: Jun. 8, 2010

(54) MONOCLONAL ANTIBODIES AGAINST $\beta_3$ INTEGRINS

(75) Inventors: Heyu Ni, North York (CA); Guangheng Zhu, Mississauga (CA)

(73) Assignee: Canadian Blood Services, Ottawa (CA)

( * ) Notice: Subject to any disclaimer, the term of this patent is extended or adjusted under 35 U.S.C. 154(b) by 0 days.

(21) Appl. No.: 12/082,686

(22) Filed: Apr. 11, 2008

(65) Prior Publication Data

US 2009/0047290 A1    Feb. 19, 2009

Related U.S. Application Data

(60) Provisional application No. 60/955,957, filed on Aug. 15, 2007.

(51) Int. Cl.
*A61K 39/395* (2006.01)
*C07K 16/28* (2006.01)
*C12N 5/10* (2006.01)
*G01N 33/53* (2006.01)

(52) U.S. Cl. .............. 424/153.1; 424/130.1; 424/141.1; 424/143.1; 424/144.1; 424/173.1; 435/7.1; 435/334; 435/343; 435/346; 530/387.1; 530/388.1; 530/388.22; 530/388.7

(58) Field of Classification Search ........................ None
See application file for complete search history.

(56) References Cited

U.S. PATENT DOCUMENTS 5,766,591 A    6/1998  Brooks et al.
6,951,645 B2  10/2005  Ruan et al.

FOREIGN PATENT DOCUMENTS

WO    WO01/21196    3/2001

OTHER PUBLICATIONS

European Patent Office Extended European Search Report corresponding to European Patent Application No. 08153880.3-2402 dated Aug. 8, 2008.
International Search Report corresponding to International Application No. PCT/US00/26095 dated Jan. 9, 2001.
Mould, Paul A., et al., Evidence that monoclonal antibodies directed against the integrin beta subunit plexin/semaphorin/integrin domain stimulate function by inducing receptor extension. *The Journal of Biological Chemistry*. vol. 280, No. 6. pp. 4238-4246. (Feb. 2005).
Ni, H., et al., Integrin activation by dithiothreitol or Mn2+ induces a ligand-occupied conformation and exposure of a novel NH2-terminal regulatory site on the beta1 integrin chain. *The Journal of Biological Chemistry*. vol. 273, No. 14. pp. 7981-7987. (Apr. 1998).
Peterson, Julie A., et al., A site involving the "hybrid" and PSI homology domains of GPIIIa (beta 3-integrin subunit) is a common target for antibodies associated with quinine-induced immune thrombocytopenia. *Blood*. vol. 101, No. 3. pp. 937-942. (Feb. 2003).
Xiao, Tsan, et al., Structural basis for allostery in integrins and binding to fibrinogen-mimetic therapeutics. *Nature*. vol. 432, No. 7013. pp. 59-67. (Nov. 2004).
Zhu, Guangheng, et al., Novel mouse anti-mouse beta 3 integrin monoclonal antibodies: Development, and characterization of new reagents for research in thrombosis and thrombocytopenia. *Blood*. vol. 110, No. 11. p. 627A. (Nov. 2007).
Beglova et al., *Cysteine-Rich Module Structure Reveals a Fulcrum for Integrin Rearrangement upon Activation*. Nature Structural Biology. vol. 9, No. 4 pp. 282-287 (2002).
Behan, M.W.H and Storey, R.F., *Antiplatelet Therapy in Cardiovascular Disease*. Postgrad. Med. J. vol. 80, pp. 155-164 (2004).
Bennett, *Structure and Function of the Platelet Integrin $\alpha_{IIb}\beta_3$*. The Journal of Clinical Investigation. vol. 115, No. 12 pp. 3363-3369 (2005).
Calvete, Juan, *Minireview - Platelet Integrin GPIIb/IIIa: Structure-Function Correlations. An Update and Lessons from Other Integrins*. Platelet Integrin GPIIB/IIIA. pp. 29-38 (update to previously published paper in Proc. Soc. Exp. Biol. Med. 208:346-360, 1995).
Cluzel et al., *The Mechanisms and Dynamics of $\alpha v \beta 3$ Integrin Clustering in Living Cells*. Journal of Cell Biology. vol. 171 pp. 383-392 (2005).
Filizola et al., *Mechanistic Insights from a Refined Three-Dimensional Model of Integrin $\alpha_{IIb}\beta_3$*. The Journal of Biological Chemistry. vol. 279, No. 23 pp. 24624-24630 (2004).
Litvinov et al., *Multi-Step Fibrinogen Binding to the Integrin $\alpha_{IIb}\beta_3$ Detected Using Force Spectroscopy*. Biophysical Journal. vol. 89 pp. 2824-2834 (2005).

(Continued)

*Primary Examiner*—Phillip Gambel
(74) *Attorney, Agent, or Firm*—Jenkins, Wilson, Taylor & Hunt, P.A.

(57) ABSTRACT

Monoclonal antibodies prepared against platelet $\beta_3$ integrin useful in antithrombotic therapy or in models of thrombosis, thrombocytopenia, and anti-angiogenesis. The antibodies are prepared using $\beta_3$ integrin deficient ($\beta_3^{-/-}$) mice immunized against platelets or $\beta_3$ integrin fragments.

23 Claims, 22 Drawing Sheets

OTHER PUBLICATIONS

Ni et al., *A Novel Murine Model of Fetal and Neonatal Alloimmune Thrombocytopenia: Response to Intravenous IgG Therapy.* Blood. vol. 107, No. 7 pp. 2976-2983 (2006).

Ni et al., *Persistence of Platelet Thrombus Formation in Arterioles of Mice Lacking Both von Willebrand Factor and Fibrinogen.* The Journal of Clinical Investigation. vol. 106, No. 3 pp. 385-392 (2000).

Webster et al., *Relative efficacy of intravenous immunoglobin G in ameliorating thrombocytopenia induced by antiplatelet GPIIbIIIa versus GPIbα antibodies.* Blood. vol. 108, No. 3 pp. 943-946 (2006).

Yang et al., *Fibrinogen and von Willebrand Factor-Independent Platelet Aggregation In Vitro and In Vivo.* Journal of Thrombosis and Haemostasis. vol. 4 pp. 2230-2237 (2006).

FIG_5

FIG_6

FIG_7

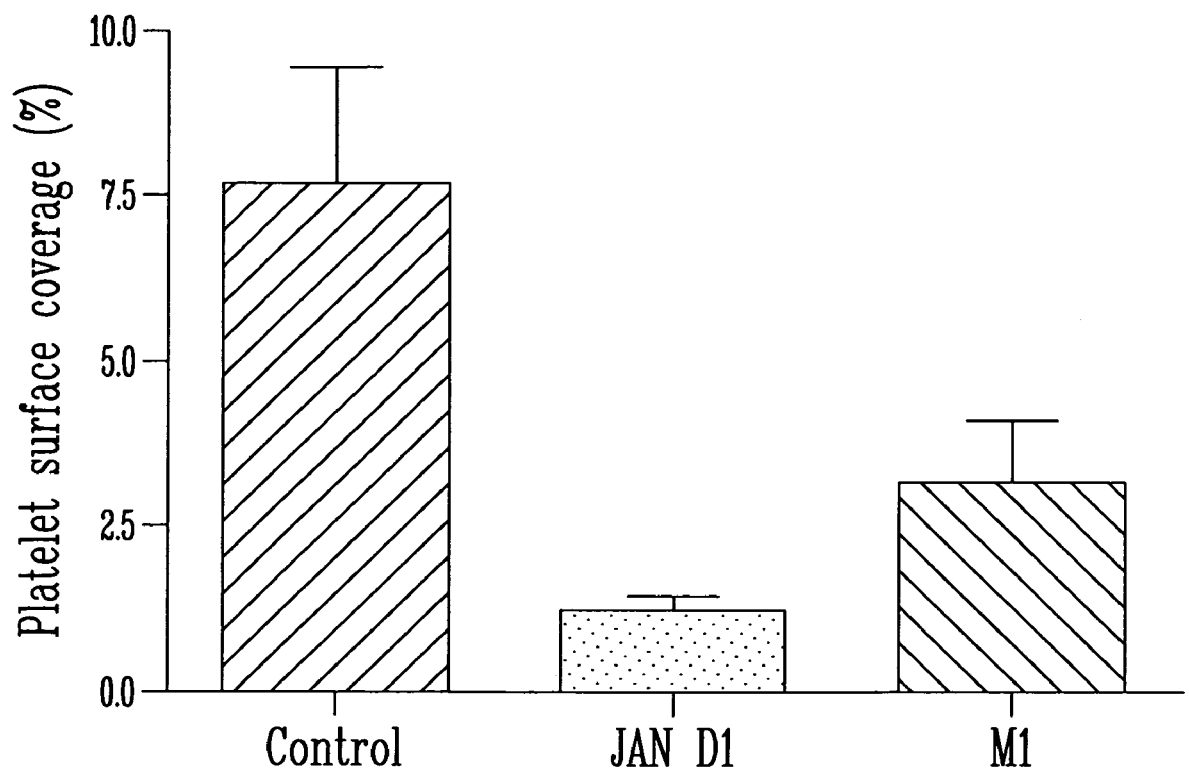
FIG_12

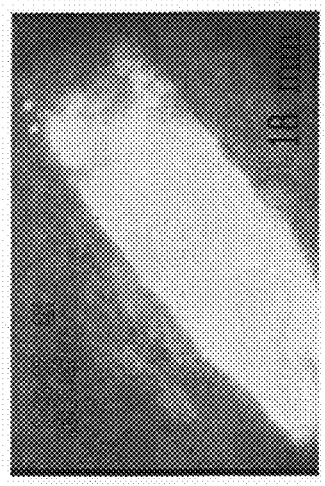 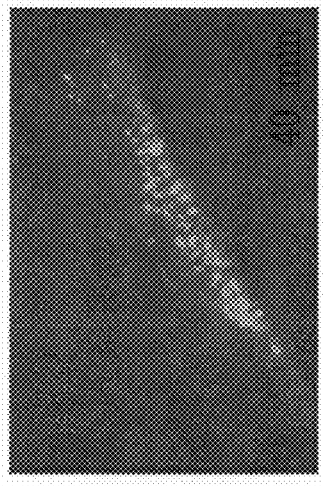 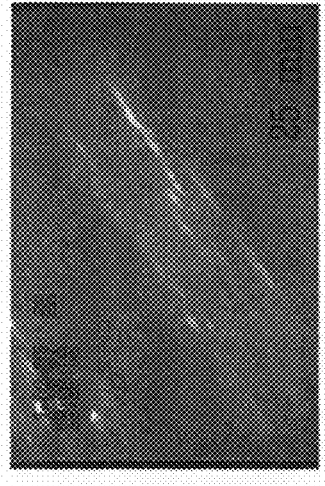
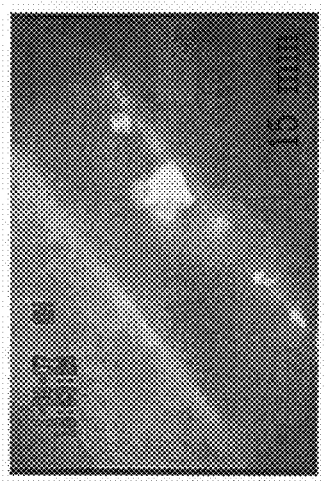 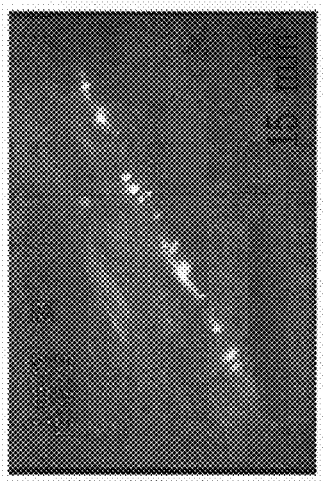 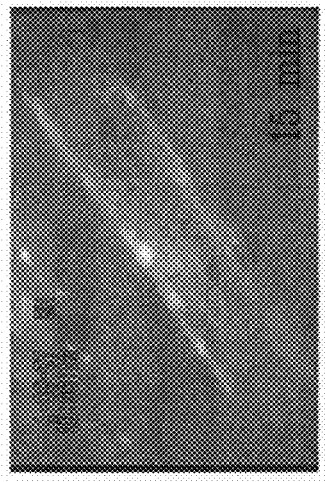
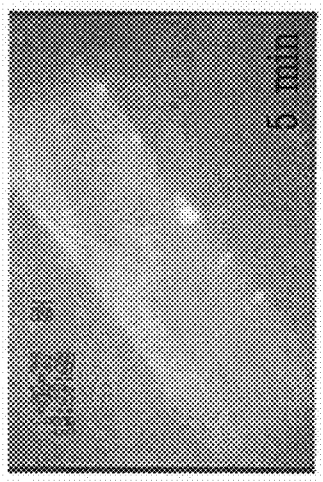 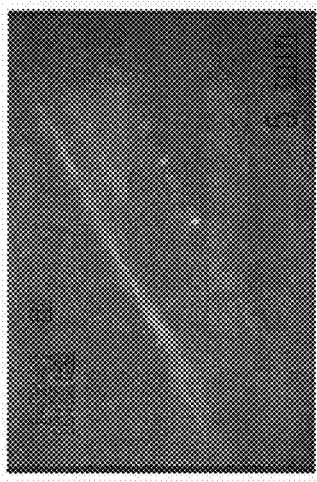 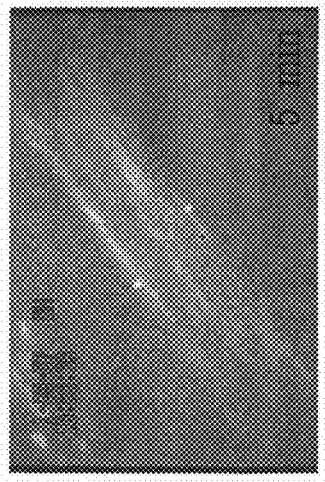
FIG. 13A     FIG. 13B     FIG. 13C

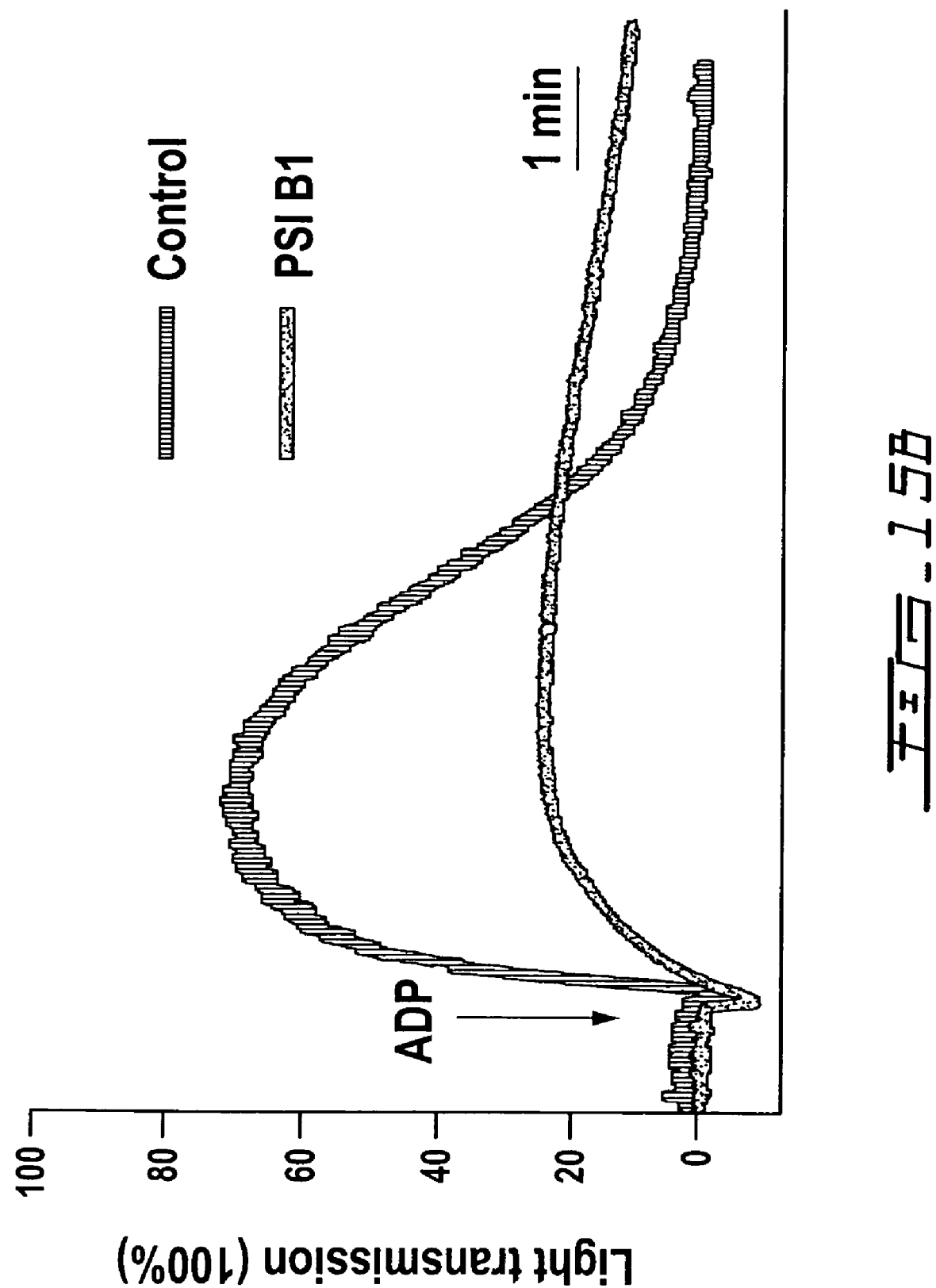

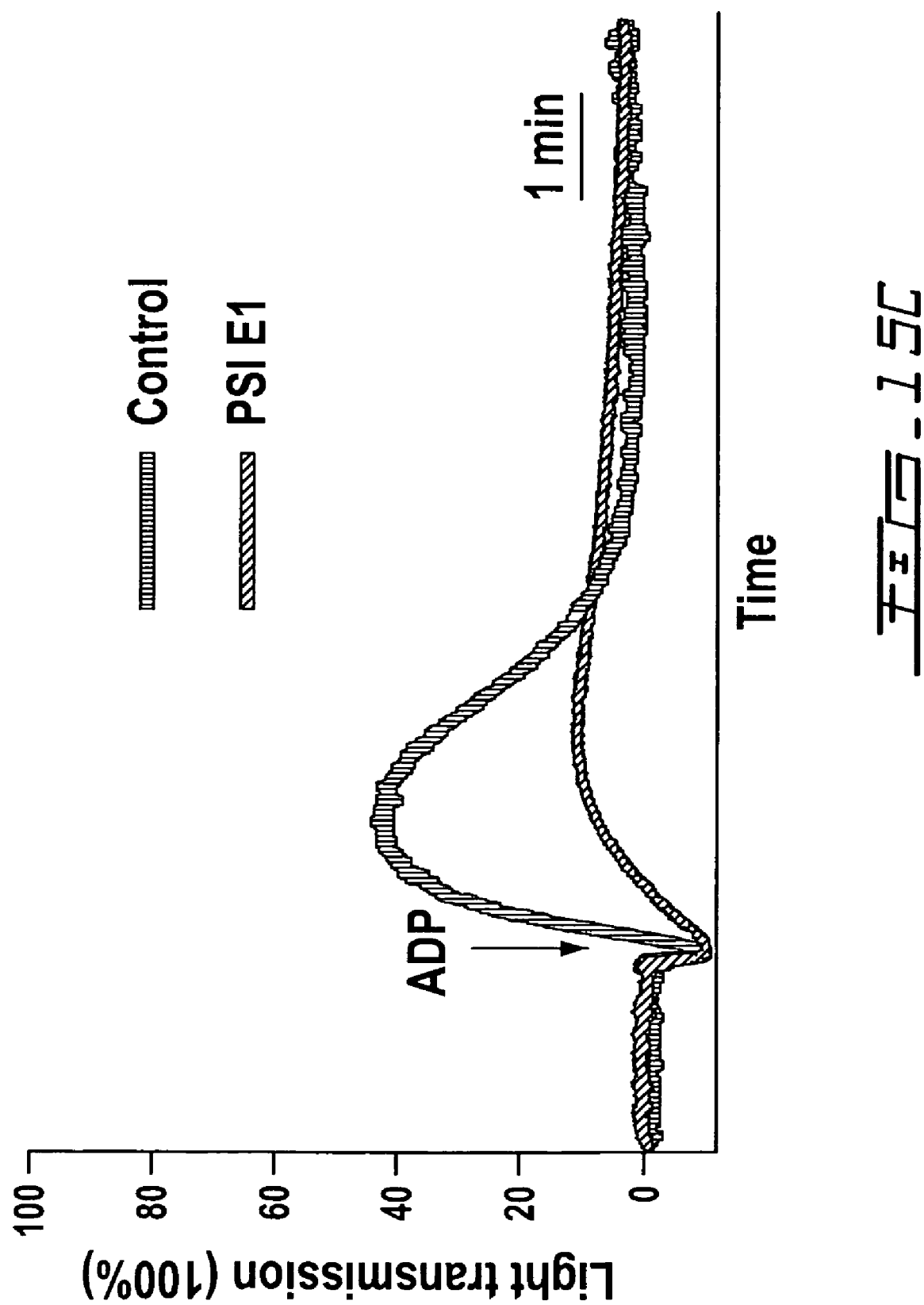

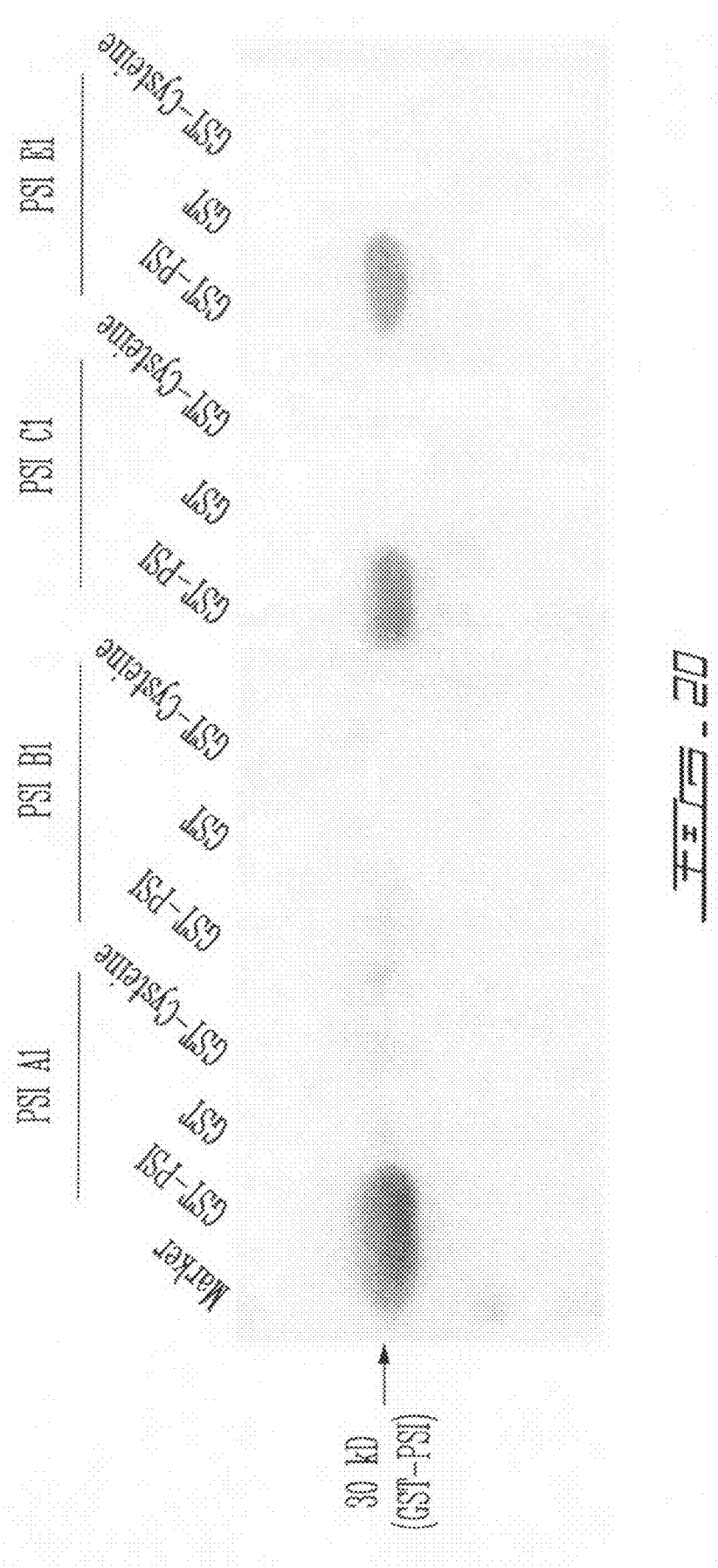

MONOCLONAL ANTIBODIES AGAINST $\beta_3$ INTEGRINS

RELATED APPLICATIONS

The presently disclosed subject matter claims the benefit of U.S. Provisional Patent Application Ser. No. 60/955,957, filed Aug. 15, 2007, the disclosure of which is incorporated herein by reference in its entirety.

TECHNICAL FIELD

The invention relates to monoclonal antibodies, and more specifically, to monoclonal antibodies against $\beta_3$ integrin useful, for instance, in antithrombotic therapy or in models of thrombosis, thrombocytopenia, and anti-angiogenesis.

BACKGROUND

Platelet adhesion and aggregation at sites of vascular injury are key events required to arrest bleeding. However, the same haemostatic processes can also lead to thrombi within atherosclerotic arteries (i.e., coronary or cerebral arteries), which is the leading cause of morbidity and mortality worldwide. Unstable angina and myocardial infarction typically result from platelet adhesion and aggregation at the site of atherosclerotic lesions in coronary arteries. Antiplatelet therapies therefore provide a useful approach to mitigate platelet aggregation, thrombus formation, and hence, the risk of suffering a heart attack or stroke.

Currently available antiplatelet agents include ASPIRIN™, the thienopyridines (ticlopidine and clopidogrel), dipyridamole, and the platelet integrin $\alpha_{IIb}\beta_3$ (glycoprotein IIb/IIIa) receptor antagonists. The present invention relates to the latter category of antiplatelet agents, namely, the platelet $\alpha_{IIb}\beta_3$ receptor antagonists.

Integrin $\alpha_{IIb}\beta_3$, a calcium-dependent heterodimer containing a $\alpha_{IIb}$ subunit and a $\beta_3$ subunit, is the most abundant platelet adhesion receptor. There are 5-12×10$^4$ copies of $\alpha_{IIb}\beta_3$ expressed on each platelet, which accounts for approximately 17% of the total platelet membrane protein. It is a receptor for fibrinogen, fibronectin, vitronectin, von Willebrand factor, and thrombospondin, and mediates platelet aggregation, firm adhesion, and spreading. Mutations in either the $\alpha_{IIb}$ or the $\beta_3$ subunit have been found to result in Glanzmann thrombasthenia, an autosomal recessive bleeding disorder affecting platelet function (Bellucci, S., and Caen, J. (2002) Blood Rev. 16, 193-202).

The $\beta_3$ subunit (GPIIa) of the complex is encoded by the ITGB3 gene, while the $\alpha_{IIb}$ subunit (GPIIb) is encoded by the ITGA2B gene. Each subunit has been extensively studied individually, as the $\alpha_{IIb}\beta_3$ heterodimeric complex belongs to a class of cell adhesion molecule receptors that share common heterodimeric structures with alpha and beta subunits.

GPIIIa is the common $\beta$ subunit of 2 integrins: $\alpha_{IIb}\beta_3$ complex and $\alpha_v\beta_3$ complex, which have distinctive alpha subunits (i.e., $\alpha_{IIb}$ and $\alpha_v$). $\alpha_v\beta_3$ is also a receptor for fibronectin, vitronectin, von Willebrand factor, and thrombospondin. Both $\alpha_{IIb}\beta_3$ integrin and $\alpha_v\beta_3$ integrin are expressed on the platelet surface although the copies of $\alpha_v\beta_3$ integrin (2-4,000/platelet) are significantly fewer. Interestingly, $\alpha_v\beta_3$ integrin is also expressed on angiogenic endothelial cells and is required for new vessel development (angiogenesis) (Brooks P C et al, 1994. Science 264:569-571). Therefore, anti-$\beta_3$ integrin antibodies may also have anti-angiogenic potential for tumor therapy.

Both integrin $\alpha$ and $\beta$ subunits contribute to their ligand (e.g., fibrinogen, fibronectin) binding. The ligand binding pocket is formed by an N-terminal $\beta$ propeller domain of the $\alpha$ subunit and the $\beta$A domain of the $\beta$ subunit (top of FIG. 1). Three Ca$^{2+}$ and one Mg$^{2+}$ have been proposed in the $\beta$ propeller domain of the $\alpha$ subunit; these divalent cations support one ligand binding site on this subunit. One divalent cation binding site has been proposed in the $\beta$A domain (vWF A domain-like domain) of the $\beta$ subunit; this domain contains an RGD peptide binding site in the up-face of a Rossman fold structure. The RGD (arginine-glycine-aspartic acid) sequence in ligands (e.g., fibrinogen, vWF, fibronectin, vitronectin, prothrombin, etc.) is the recognition motif of the integrin family, and after ligand binding, some divalent cations may be replaced by an RGD portion of the ligands, but divalent cations are required to maintain the specific structure for ligand binding in most cases.

It is notable that many anti-PSI domain antibodies, if not all, may activate integrins by directly changing the integrin conformation. Based on earlier studies (Ni H et al, J Biol Chem. Apr. 3, 1998; 273(14):7981-7987), and the integrin structure model (Xiao T et al, Nature. Nov. 4, 2004; 432 (7013):59-67), antibody binding to the PSI domain of integrin (e.g., $\beta_3$ integrin) may enhance the "swinging out" of the leg of the $\beta$ subunit and facilitate integrin-ligand binding. Therefore, anti-PSI domain of $\beta$3 integrin antibodies may lead to platelet activation and aggregation, and have therapeutic potential to stop bleeding.

Among the commercially available platelet $\alpha_{IIb}\beta_3$ receptor antagonists is the monoclonal antibody (mAb) 7E3, which binds to the $\alpha_{IIb}\beta_3$ receptor on the platelet. A humanized form of 7E3 is the active agent in the clinical drug REOPRO™ (abciximab), a drug developed for the treatment of thrombotic diseases. According to the REOPRO™ website, the drug blocks interaction of fibrinogen with $\alpha_{IIb}\beta_3$, and hence the final common pathway to platelet aggregation. REOPRO™ (abciximab) is thus claimed to block the formation of platelet aggregates and the formation of an arterial thrombus, and is used as an adjunct to percutaneous coronary intervention (PCI).

Another commercially available platelet $\alpha_{IIb}\beta_3$ receptor antagonist, tirofiban, is marketed as a drug in many countries under the brand name AGGRASTAT™. Tirofiban is a non-peptide $\alpha_{IIb}\beta_3$ receptor inhibitor, and is usually used in combination with heparin to help prevent blood clotting that occurs during certain heart conditions (e.g., acute coronary syndrome), or in medical procedures such as percutaneous coronary intervention (PCI).

Eptifibatide (INTEGRILIN™), another $\alpha_{IIb}\beta_3$ receptor antagonist, is an intravenous cyclical heptapeptide derived from a protein found in the venom of the southeastern pygmy rattlesnake (*Sistrurus millarus barbouri*). It has been shown to be efficacious in the treatment of patients during coronary angioplasty, myocardial infarction and angina.

A significant drawback of these $\alpha_{IIb}\beta_3$ antagonists, however, is the occurrence of side-effects, such as bleeding disorders. Due to the severity of these side effects, there is a need for continued research with a view towards developing new platelet aggregation inhibitors that can be safely used for antithrombotic therapy.

SUMMARY

This Summary lists several embodiments of the presently disclosed subject matter, and in many cases lists variations and permutations of these embodiments. This Summary is merely exemplary of the numerous and varied embodiments.

Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

An object of the invention is to provide pharmaceutical compositions for inhibiting platelet aggregation and thrombosis, as well as methods for inhibiting platelet aggregation and inhibiting thrombosis. Another object is to provide antibodies specific for $\beta_3$ integrin, pharmaceutical and diagnostic uses therefor and compositions comprising same.

As an aspect of the invention there is provided the following hybridoma cell lines deposited under the terms of the Budapest Treaty with the International Depositary Authority of Canada (IDAC), National Microbiology Laboratory, Public Health Agency of Canada, 1015 Arlington Street, Winnipeg, Manitoba Canada R3E 3R2, under the following Accession Nos.:

| mAbs | Hybridoma Cell Line Deposited Under Accession No. | Deposit Date |
| --- | --- | --- |
| 9D2 | 230507-03 | 23 May, 2007 |
| M1 | 230507-01 | 23 May, 2007 |
| JAN A1 | 230507-02 | 23 May, 2007 |
| JAN B1 | 230507-08 | 23 May, 2007 |
| JAN C1 | 190607-03 | 19 Jun., 2007 |
| JAN D1 | 190607-05 | 19 Jun., 2007 |
| DEC A1 | 190607-01 | 19 Jun., 2007 |
| DEC B1 | 190607-02 | 19 Jun., 2007 |
| PSI A1 | 230507-04 | 23 May, 2007 |
| PSI B1 | 230507-05 | 23 May, 2007 |
| PSI C1 | 230507-06 | 23 May, 2007 |
| PSI E1 | 230507-07 | 23 May, 2007 |

All restrictions imposed by the depositor on the availability to the public of the deposited material will be irrevocably removed upon the granting of a U.S. patent.

As another aspect, there is provided an isolated and purified antibody produced by a hybridoma cell line having IDAC Accession No. selected from 230507-03, 230507-01, 230507-02, 230507-08, 190607-03, 190607-05, 190607-01, 190607-02, 230507-04, 230507-05, 230507-06 and 230507-07, an antibody having the antigen binding fragment thereof, or a fragment of the antibody produced by the hybridoma cell line which binds platelet integrin $\beta_3$.

In an embodiment, the antibody or antigen binding fragment is humanized.

As a further aspect, there is provided a monoclonal antibody selected from 9D2, M1, JAN A1, JAN B1, JAN C1, JAN D1, DEC A1, DEC B1, PSI A1, PSI B1, PSI C1 and PSI E1, respectively produced by a hybridoma cell line having IDAC Accession No. 230507-03, 230507-01, 230507-02, 230507-08, 190607-03, 190607-05, 190607-01, 190607-02, 230507-04, 230507-05, 230507-06 and 230507-07.

As a further aspect, there is provided a pharmaceutical composition comprising the isolated and purified antibody, antibody fragment, or monoclonal antibody described above, and a pharmaceutical acceptable carrier. In an embodiment the pharmaceutical composition is for inhibiting platelet aggregation. In another embodiment the pharmaceutical composition is for antithrombotic treatment. In a further embodiment the pharmaceutical composition is for platelet activation. In another embodiment the pharmaceutical composition is for inhibition of angiogenesis.

As yet another aspect, there is provided a solid phase having attached thereto the isolated and purified antibody, antibody fragment, or monoclonal antibody as described above. The solid phase is particularly useful for separation or isolation of $\beta_3$ integrin. In an embodiment, the solid phase may comprise a gel, a hydrogel, a resin, a bead, nitrocellulose, a nylon membrane, a micrometer plate, a culture flask, or a polymeric material.

As another aspect, there is provided a purified antibody, antibody fragment, or monoclonal antibody as described above, labeled with a detectable marker or conjugate. In an embodiment, said detectable marker is a fluorescent or radioactive marker. In another embodiment, said conjugate is biotin, or an enzyme such as peroxidase or alkaline phosphatase.

As yet another aspect, there is provided a diagnostic method for measuring $\beta_3$ integrin expression, said method comprising obtaining an integrin positive cell sample and measuring $\beta_3$ integrin expression with an antibody produced by the hybridoma cell line having IDAC Accession No. 230507-03, 230507-01, 230507-02, 230507-08, 190607-03, 190607-05, 190607-01, 190607-02, 230507-04, 230507-05, 230507-06 and 230507-07, an antibody having the antigen binding fragment thereof, or a fragment of the antibody produced by the hybridoma cell line which binds platelet integrin $\beta_3$. The integrin positive cell sample may be any sample of cellular material in which $\beta_3$ integrin may be expressed, and whereby it would be desirable to measure or monitor integrin expression, including for instance platelets, macrophages, leukocytes, or new growth endothelial cells.

As a further aspect, there is provided a diagnostic method for measuring platelet count, said method comprising obtaining a platelet sample and measuring platelet count with an antibody produced by the hybridoma cell line having IDAC Accession No. 230507-03, 230507-01, 230507-02, 230507-08, 190607-03, 190607-05, 190607-01, 190607-02, 230507-04, 230507-05, 230507-06 and 230507-07, an antibody having the antigen binding fragment thereof, or a fragment of the antibody produced by the hybridoma cell line which binds platelet integrin $\beta_3$.

In another aspect, there is provided a diagnostic method for tracking platelets in vivo, said method comprising administering an antibody produced by the hybridoma cell line having IDAC Accession No. 230507-03, 230507-01, 230507-02, 230507-08, 190607-03, 190607-05, 190607-01, 190607-02, 230507-04, 230507-05, 230507-06 and 230507-07, an antibody having the antigen binding fragment thereof, or a fragment of the antibody produced by the hybridoma cell line which binds platelet integrin $\beta_3$, said antibody or antibody fragment comprising a label, and tracking said labeled antibody or antibody fragment in vivo in a mammal.

In yet a further aspect there is provided a method of antithrombotic treatment comprising administering a composition comprising an antibody produced by the hybridoma cell line having IDAC Accession No. 230507-03, 230507-01, 230507-02, 230507-08, 190607-03, 190607-05, 190607-01, 190607-02, 230507-04, 230507-05, 230507-06 and 230507-07, an antibody having the antigen binding fragment thereof, or a fragment of the antibody produced by the hybridoma cell line which binds platelet integrin $\beta_3$, and an acceptable carrier.

In yet another aspect there is provided a method of inhibiting platelet aggregation comprising administering a composition comprising an antibody produced by the hybridoma cell line having IDAC Accession No. 230507-03, 230507-01, 230507-02, 230507-08, 190607-03, 190607-05, 190607-01, 190607-02, 230507-04, 230507-05, 230507-06 and 230507-07, an antibody having the antigen binding fragment thereof, or a fragment of the antibody produced by the hybridoma cell line which binds platelet integrin $\beta_3$, and an acceptable carrier.

There is further provided a method of platelet activation comprising administering a composition comprising an antibody produced by the hybridoma cell line having IDAC Accession No. 230507-03, 230507-01, 230507-02, 230507-08, 190607-03, 190607-05, 190607-01, 190607-02, 230507-04, 230507-05, 230507-06 and 230507-07, an antibody having the antigen binding fragment thereof, or a fragment of the antibody produced by the hybridoma cell line which binds platelet integrin $\beta_3$, and an acceptable carrier.

In addition, as an aspect of the invention there is provided a method for inhibition of angiogenesis comprising administering a composition comprising an antibody produced by the hybridoma cell line having IDAC Accession No. 230507-03, 230507-01, 230507-02, 230507-08, 190607-03, 190607-05, 190607-01, 190607-02, 230507-04, 230507-05, 230507-06 and 230507-07, an antibody having the antigen binding fragment thereof, or a fragment of the antibody produced by the hybridoma cell line which binds platelet integrin $\beta_3$, and an acceptable carrier.

BRIEF DESCRIPTION OF THE FIGURES

Further features and advantages of the present invention will become apparent from the following detailed description, taken in combination with the appended drawings in which:

FIG. 12 is a graphical representation of % platelet surface coverage for the collagen surfaces shown in FIG. 11. Whole human blood treated with JAN D1 and M1 significantly decreased the percentage of surface coverage by platelets (**P<0.004, *P<0.05);

FIG. 13 illustrates thrombus formation in wild type control mice in the absence of mAb treatment (control, A), and with treatment using anti-mouse $\beta_3$ integrin mAbs JAN D1 (B) and M1 (C). In WT C57BL/6 control mice, single fluorescent platelets started to adhere at the site of vessel injury several minutes after FeCl$_3$ injury. Visible thrombi formed and the injured arteriole occluded after 18 min. In JAN D1 and M1 (0.5 μg/g) treated mice, single platelets adhered to the site of injury and formed small aggregates but thrombus formation was significantly delayed and occlusive thrombi failed to form (n=2). Anti-β$_3$ integrin mAbs JAN D1 and M1 thus both inhibited thrombus formation. Time after FeCl$_3$ injury is indicated in the corner of each image (5, 15, and 18 min);

FIGS. 15A-15C are standard aggregometry traces of mouse platelets incubated with PBS (black), mouse anti-mouse PSI domain mAbs, PSI A1, PSI C1 (FIG. 15A), PSI B1 (FIG. 15B) or PSI E1 (FIG. 15C) (80 μg/ml), then stimulated with ADP (200 μM). Platelet aggregation (light transmission) was monitored over 12 min. All these mAbs significantly inhibited mouse platelet aggregation induced by ADP in mouse PRP.

FIG. 20 shows the results of Western blot analysis of mouse recombinant PSI protein with monoclonal mouse anti-mouse PSI domain antibodies. Briefly, recombinant PSI protein were run in each lane of a reducing 7% SDS-PAGE gel. After transfer to PVDF membrane, the membrane was immunoblotted with mouse anti-mouse PSI domain antibodies PSI A1, PSI B1, PSI C1 or PSI E1. Immunoreactive bands were developed by reaction with BCIP/NBT substrate. All anti-β3 PSI domain antibodies recognize a linear epitope in recombinant PSI protein.

DETAILED DESCRIPTION

Integrin $\alpha_{IIb}\beta_3$ is the key receptor required for platelet adhesion and aggregation, and antagonists of this receptor have potential in controlling thrombosis. Furthermore, antagonists that block $\alpha_v\beta_3$ integrin have potential use in anti-tumor therapy, since such antagonists have been shown to block angiogenesis. The common β$_3$ subunit shared between these two receptors therefore provides a useful target for generating monoclonal antibodies (mAbs) useful as antagonists of integrin $\alpha_{IIb}\beta_3$ and/or $\alpha_v\beta_3$.

Functional neutral mAbs generated against the β$_3$ subunit, which do not block platelet aggregation or angiogenesis, are also useful as reagents for patient diagnosis. Since epitopes of these functional neutral mAbs are usually constitutively expressed on the platelet surface, these mAbs can be used to measure β$_3$ integrin expression, to measure platelet count, and in other diagnostic assays such as to track platelets in vivo in patients.

Traditional methods to generate mAbs against human proteins have used wild-type BALB/c mice. The antigenicity of a human protein, and thus the ability to generate mAbs using such methods, will be based on the difference between the human and murine protein sequences. Since integrin family members are highly conserved between these two species (>80-90% identity), the repertoire of antibodies against human β$_3$ integrin in wild-type BALB/c mice is limited. The mAb 7E3 was generated via this method, and therefore this antibody does not recognize murine β$_3$ integrin.

The present inventors have generated novel mAbs by using β$_3$ integrin-deficient BALB/c mice, which do not possess β$_3$ integrin and can thus produce antibodies against any portion of β$_3$ integrin, as opposed to wild-type mice, which only produce antibodies to non-conserved regions of β$_3$ integrin. The repertoire of antibodies against β$_3$ integrin using this methodology is much larger compared to using wild-type mice since an antibody can be generated against the entire β$_3$ protein, as well as to the conformational epitopes formed by the α and β subunits of the integrin receptors ($\alpha_{IIb}\beta_3$ complex and $\alpha_v\beta_3$ complex).

Figure 1:
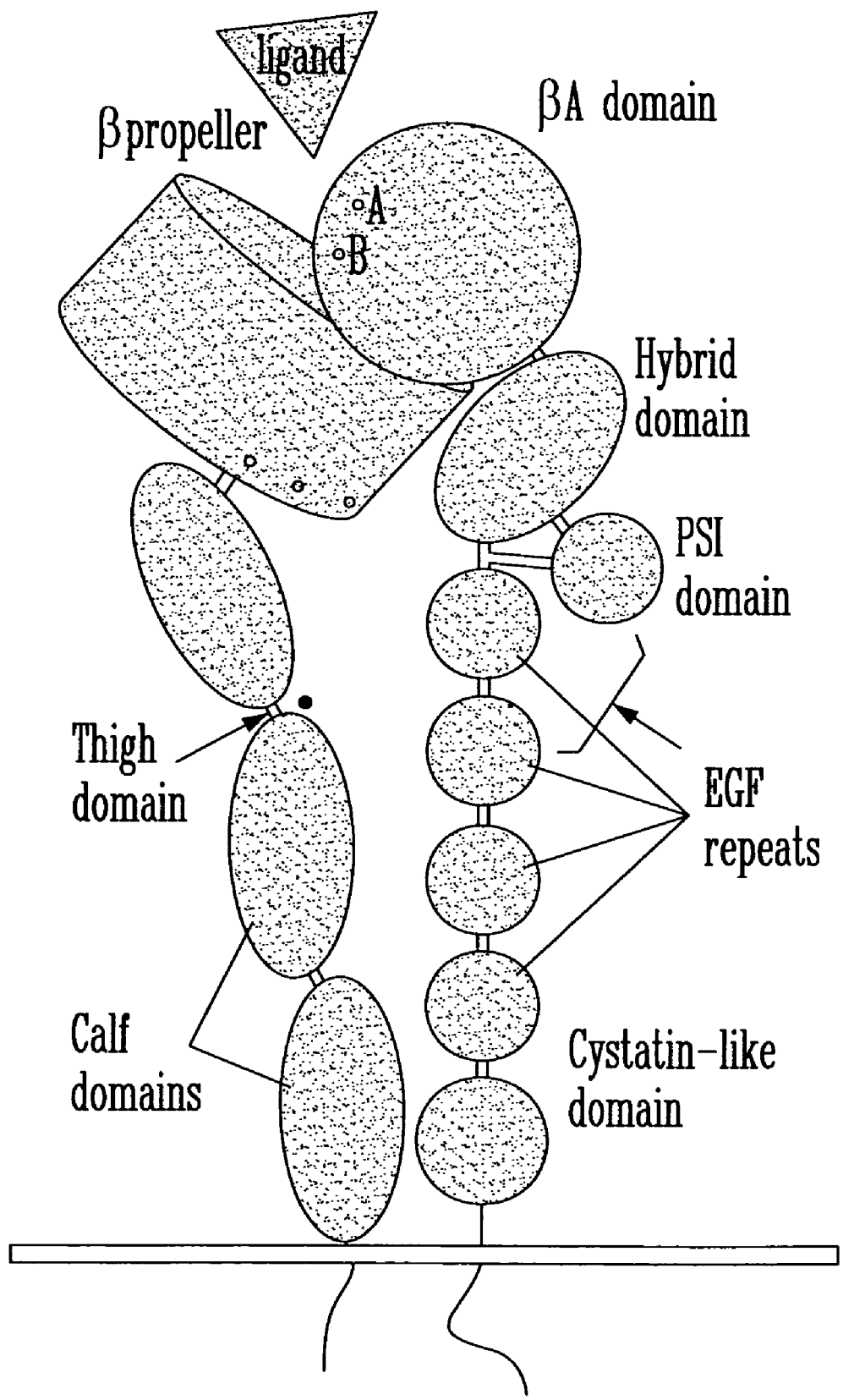
FIG. 1 is an illustration of the integrin structure (i.e., platelet $\alpha_{IIb}\beta_3$ and $\alpha_v\beta_3$ receptors)
Figure 2:
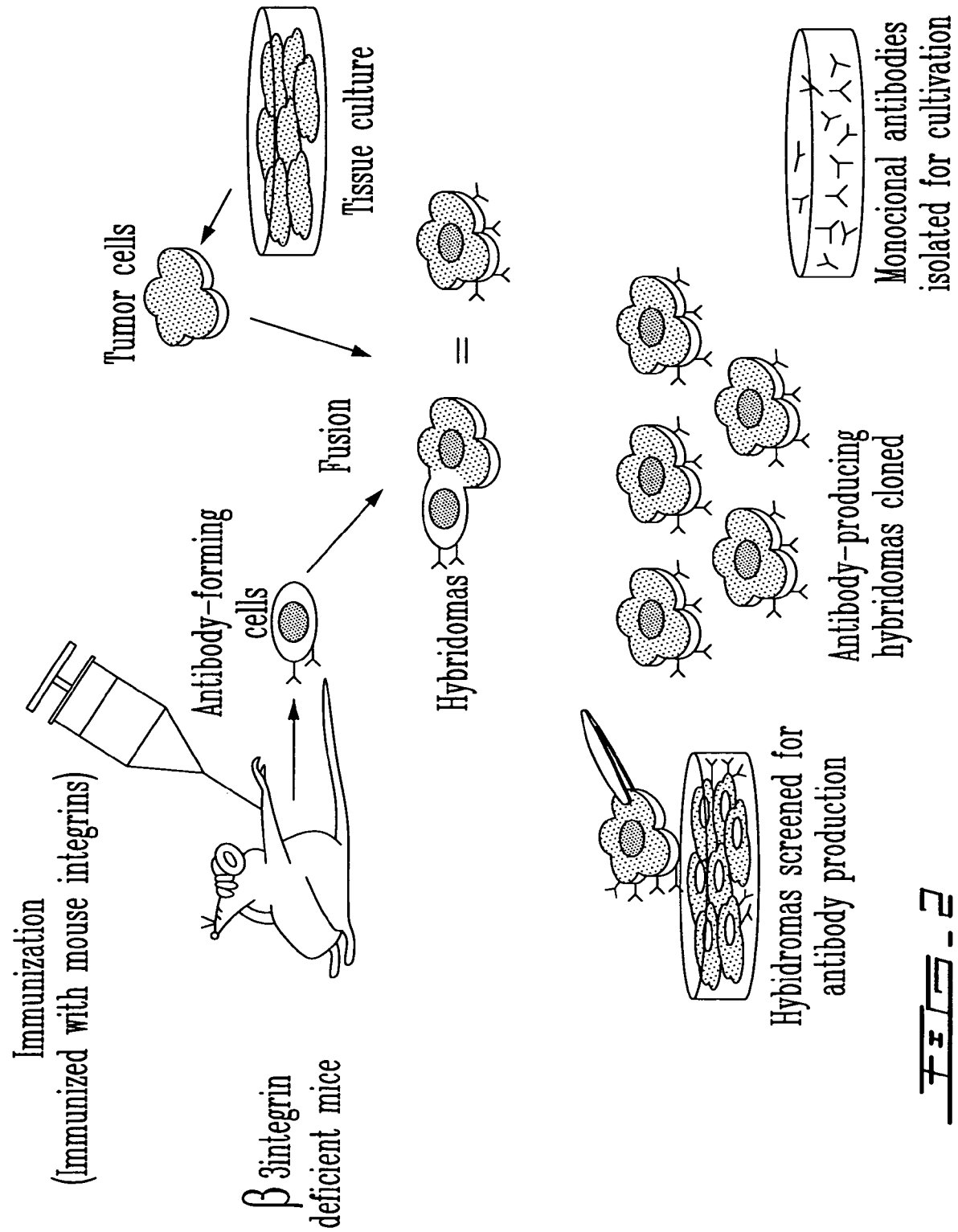
FIG. 2 is a flow diagram illustrating a method for generating monoclonal antibodies (mAbs) using $\beta_3$ integrin gene knockout mice.

Hybridomas were generated using spleens of wild-type platelet transfused β$_3$ integrin-deficient mice (FIG. 2). Twelve clones of these hybridomas were generated and analyzed, the results of which are shown in Table 1.

TABLE 1

Mouse Anti-mouse β$_3$ Integrin Monoclonal Antibodies*

| mAbs | Isotype | Specificity | Epitope | Effect on Murine Platelet Aggregation | Binding (Human Platelets) |
|---|---|---|---|---|---|
| 9D2 | IgG1 | β$_3$ integrins | Conformational | Inhibition | + |
| M1 | IgG1 | β$_3$ integrins | Conformational | Inhibition | + |
| JAN A1 | IgG1 | β$_3$ integrins | Conformational | Inhibition | − |
| JAN B1 | IgG1 | β$_3$ integrins | Conformational | Inhibition | − |
| JAN C1 | IgG1 | β$_3$ integrins | Conformational | Inhibition | + |
| JAN D1 | IgG1 | β$_3$ integrins | Conformational | Inhibition | + |
| DEC A1 | IgG3 | β$_3$ integrins | Conformational | Inhibition | + |

TABLE 1-continued

Mouse Anti-mouse $\beta_3$ Integrin Monoclonal Antibodies*

| mAbs | Isotype | Specificity | Epitope | Effect on Murine Platelet Aggregation | Binding (Human Platelets) |
|---|---|---|---|---|---|
| DEC B1 | IgG3 | $\beta_3$ integrins | Conformational | ND | + |
| PSI A1 | IgG1 | PSI domain | Linear | Inhibition | + |
| PSI B1 | IgG1 | PSI domain | Linear | Inhibition/ activation | + |
| PSI C1 | IgG1 | PSI domain | Linear | Inhibition | + |
| PSI E1 | IgG2b | PSI domain | Linear | Inhibition | + |

*$\beta_3^{-/-}$ mice were immunized with WT mouse platelets or recombinant mouse PSI domain. Isotype and binding to platelets were analyzed by a flow cytometric assay by using washed platelets pre-incubated with 10 μg/mL of mAb and then incubated with FITC-conjugated anti-mouse -IgG, -IgG1, -IgG2a, -IgG2b and IgG3. Mouse platelet aggregation was induced by ADP in mouse PRP in either the absence or presence of each anti-mouse $\beta_3$ integrin mAb.
ND = Not Determined.

Figure 4:
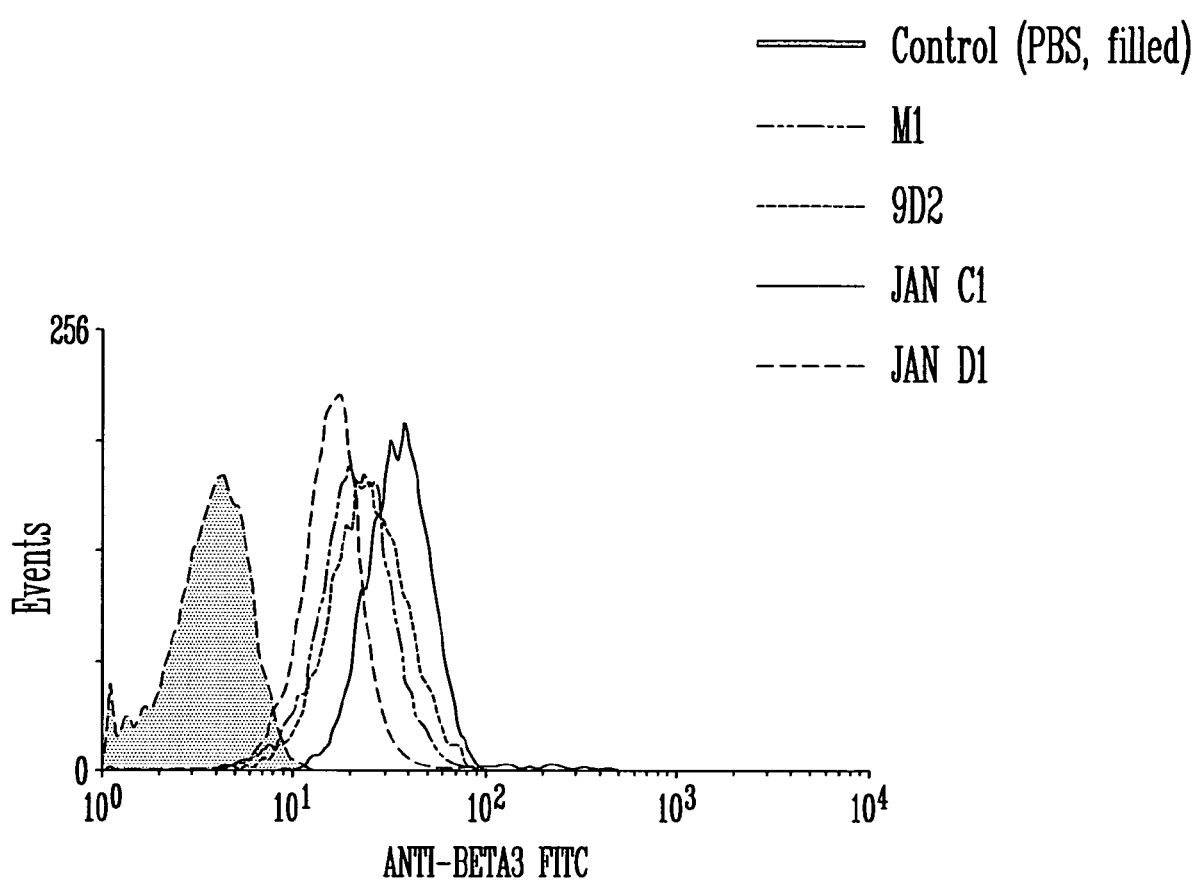
FIG. 4 is a graphical representation of the results of analysis by flow cytometry of anti-mouse $\beta_3$ integrin mAbs 9D2, M1, JAN C1 and JAN D1 binding to wild type mouse platelets. Wild Type (WT) mouse platelets were incubated with PBS (control, filled peak), 9D2, M1, JAN C1 or JAN D1 for 1 hour, then stained with FITC-labeled goat anti-mouse IgG for 45 minutes and analyzed by flow cytometry. JAN C1 has much lower affinity than JAN D1 to mouse platelets.
Figure 5:
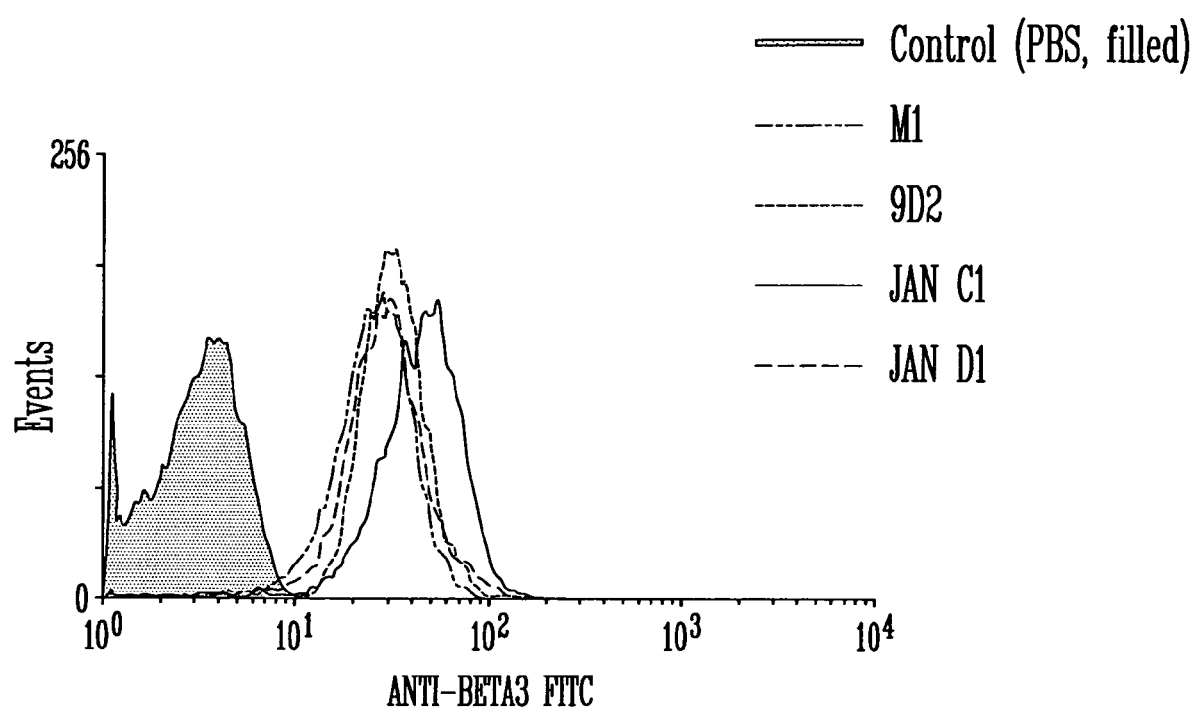
FIG. 5 is a graphical representation of the results of analysis by flow cytometry of anti-mouse $\beta_3$ integrin mAbs 9D2, M1, JAN C1 and JAN D1 binding to healthy human platelets. Human platelets were incubated with PBS (control, filled peak), 9D2, M1, JAN C1 or JAN D1 for 1 hour, then stained with FITC-labeled goat anti-mouse IgG for 45 minutes and analyzed by flow cytometry.
Figure 6:
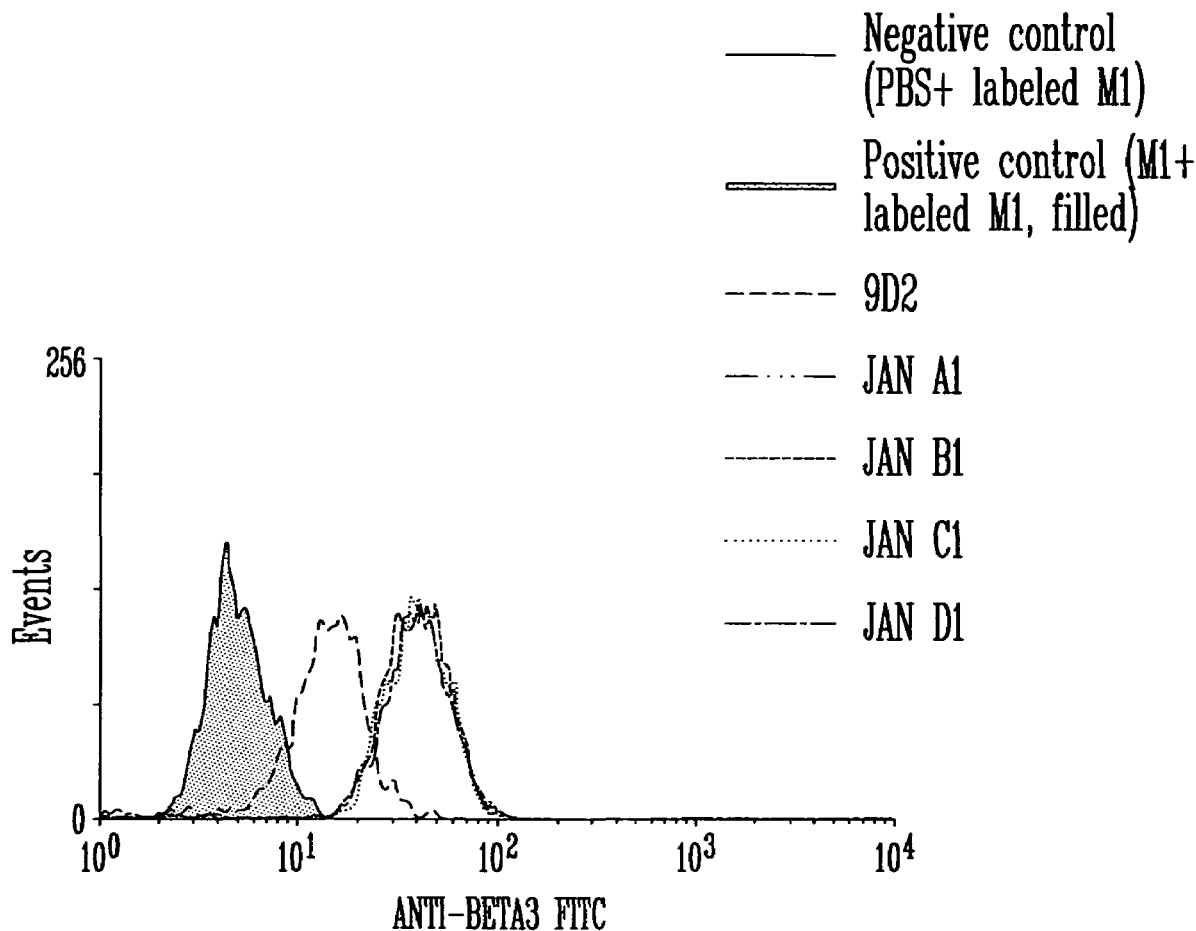
FIG. 6 is an antibody competition assay which demonstrates that the 9D2, JAN A1, JAN B1, JAN C1 and JAN D1 antibodies recognize distinct epitopes from that recognized by M1 antibody, since they do not inhibit fluorescent labeled M1 binding. Mouse platelets were incubated with PBS (negative control, black), M1 (positive control, filled peak), 9D2, JAN A1, JAN B1, JAN C1 or JAN D1 for 1 hour, then stained with fluorescent Alex-488-labeled M1 for 45 minutes and analyzed by flow cytometry. JAN A1, JAN B1, JAN C1 or JAN D1 do not inhibit labeled M1 binding to platelet, and 9D2 only inhibits partially.

As summarized above, and demonstrated in FIGS. 4 and 5 for four representative mAbs, 10 of the mAbs generated according to the described method are able to bind both human and mouse platelets, and are thus clearly distinct from 7E3 which does not recognize murine $\beta_3$ integrin. The mAbs JAN A1 and JAN B1 only bind mouse platelets, and are therefore also distinct from 7E3.

Figure 7:
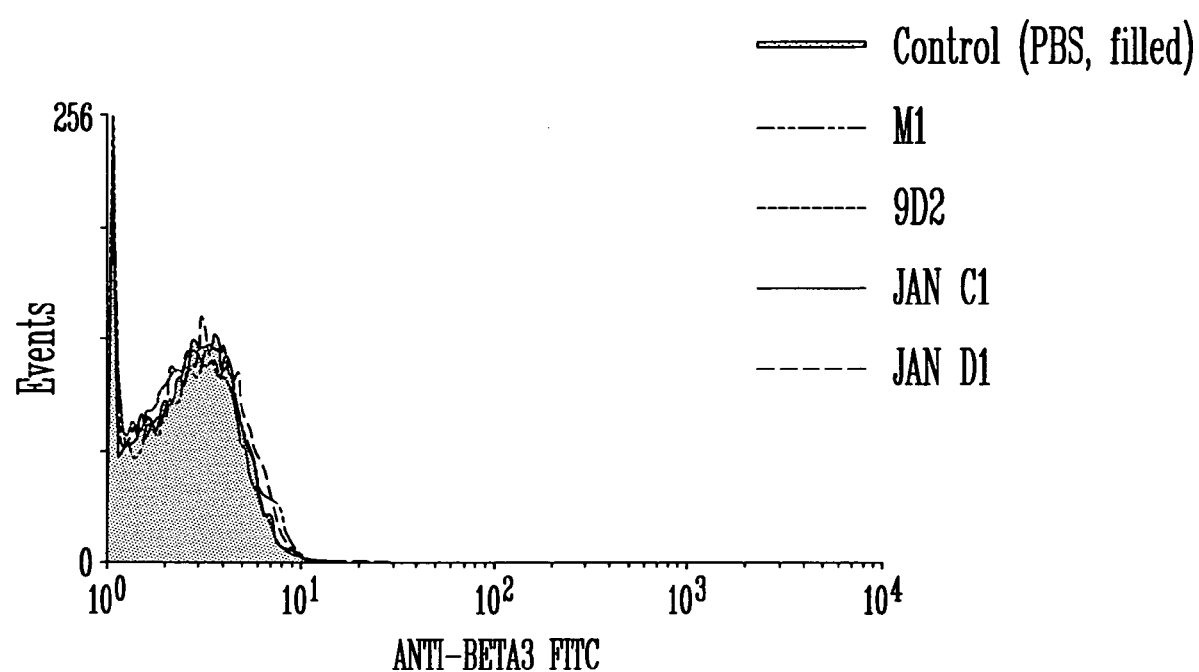
FIG. 7 is a graphical representation of the results of analysis by flow cytometry of anti-mouse $\beta_3$ integrin mAbs 9D2, M1, JAN C1 and JAN D1 binding to $\beta_3$ integrin deficient ($\beta_3^{-/-}$) mouse platelets. These mAbs did not bind platelets without $\beta_3$ integrin, which indicates that they are specific for $\beta_3$ integrin. $\beta_3$ integrin deficient ($\beta_3$−/−) mouse platelets were incubated with PBS (control, filled peak), 9D2, M1, JAN C1 or JAN D1 for 1 hour, then stained with FITC-labeled goat anti-mouse IgG for 45 minutes and analyzed by flow cytometry. All anti-mouse mAbs (including those listed in table 1 but not shown in FIG. 7) did not bind $\beta_3$−/− platelets and thus are specific to $\beta_3$ integrin.
Figure 8:
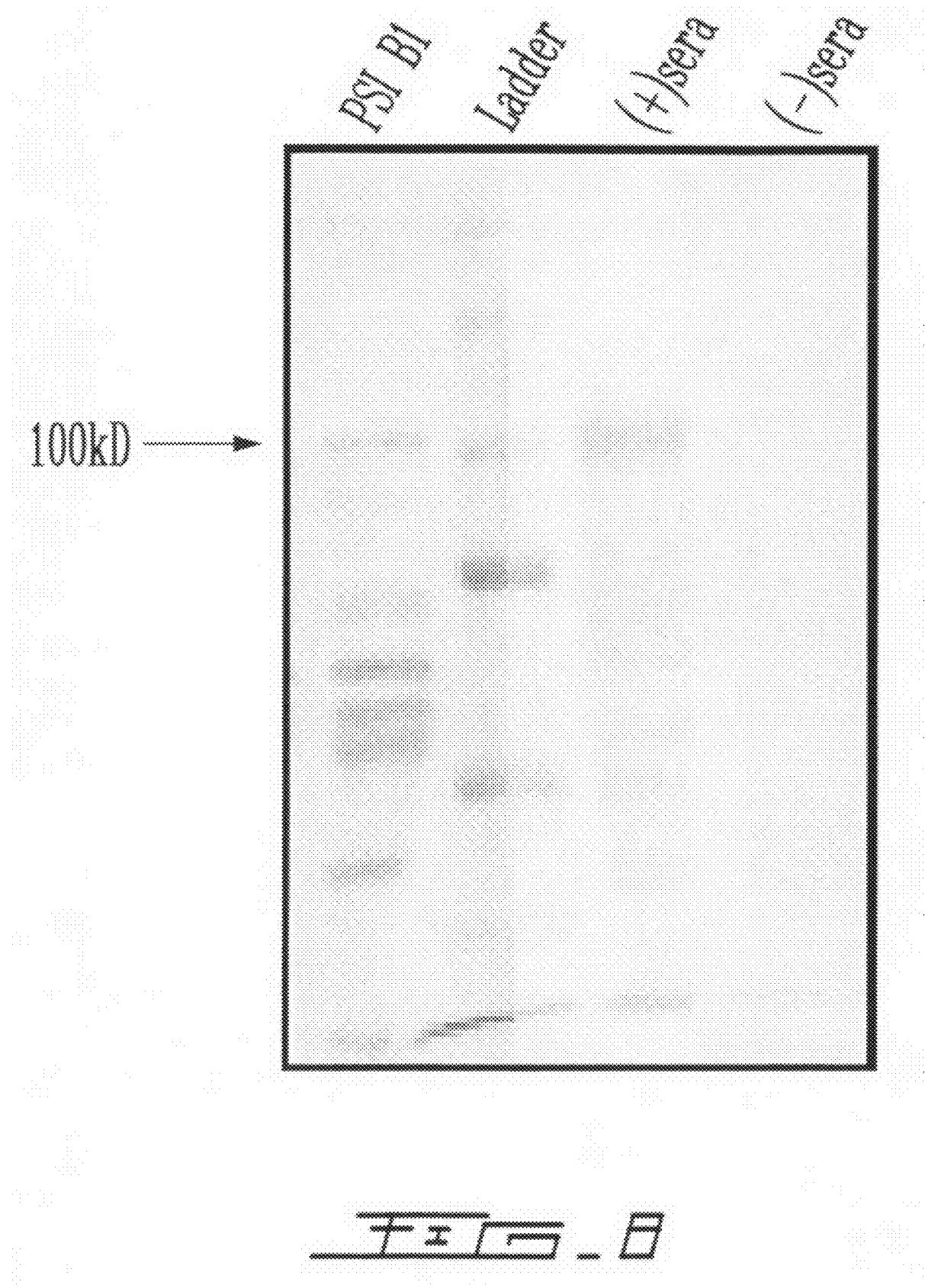
FIG. 8 illustrates the results of western blot analysis of platelet lysate with monoclonal mouse anti-mouse PSI domain antibody PSI B1. As demonstrated, anti-PSI domain mAb PSI B1 recognizes a linear PSI domain epitope. Briefly, lysate from $10^8$ WT platelets were run in each lane of a non-reducing 7% SDS-PAGE gel. After transfer to PVDF membrane, the membrane was immunoblotted with mouse anti-mouse PSI domain antibody (PSI B), a polyclonal anti-$\beta_3$ integrin antisera ((+) sera or pre-immune sera (−) sera). Immunoreactive bands were developed by reaction with BCIP/NBT substrate.

The mAbs generated are also highly specific for $\beta_3$ integrin, and some are particularly specific for the $\beta_3$ integrin PSI domain. As demonstrated in FIG. 7, which illustrates binding data with $\beta_3$ integrin deficient platelets for four of the mAbs, 9D2, M1, JAN C1 and JAN D1, none of the mAbs bound the mouse platelets without $\beta_3$ integrin.

Figure 9:
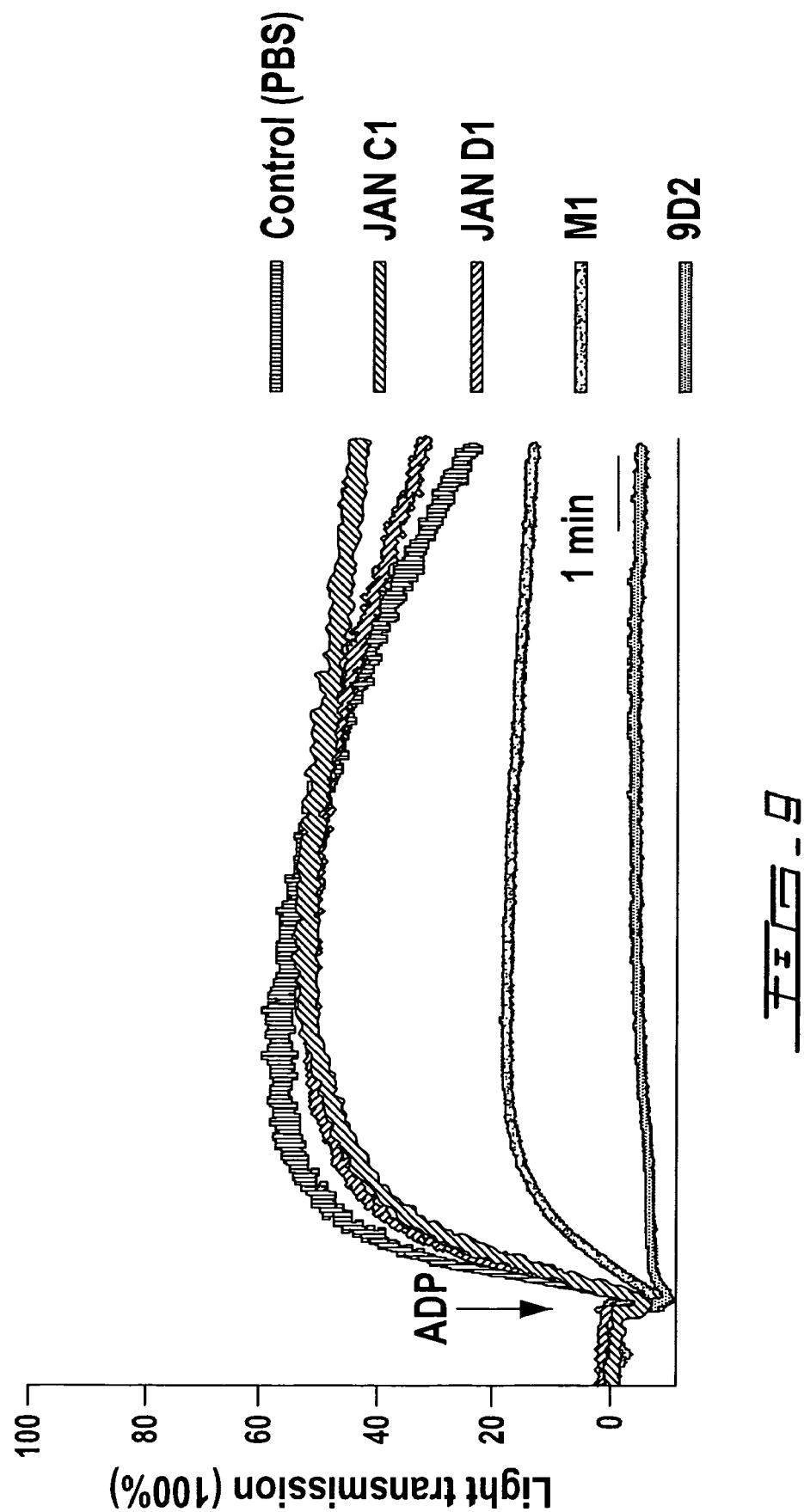
FIG. 9 is a graphical representation of the results of mouse platelet aggregation in the presence and absence of anti-mouse $\beta_3$ integrin mAbs 9D2, M1, JAN C1 and JAN D1. Mouse platelets were incubated with PBS (control, black), mouse anti-mouse $\beta_3$ integrin mAbs, 9D2, M1, JAN C1 or JAN D1 (40 μg/mL), then stimulated with ADP (20 μM). Platelet aggregation (light transmission) was monitored over 12 min. 9D2 and M1 significantly inhibited mouse platelet aggregation.
Figure 10:
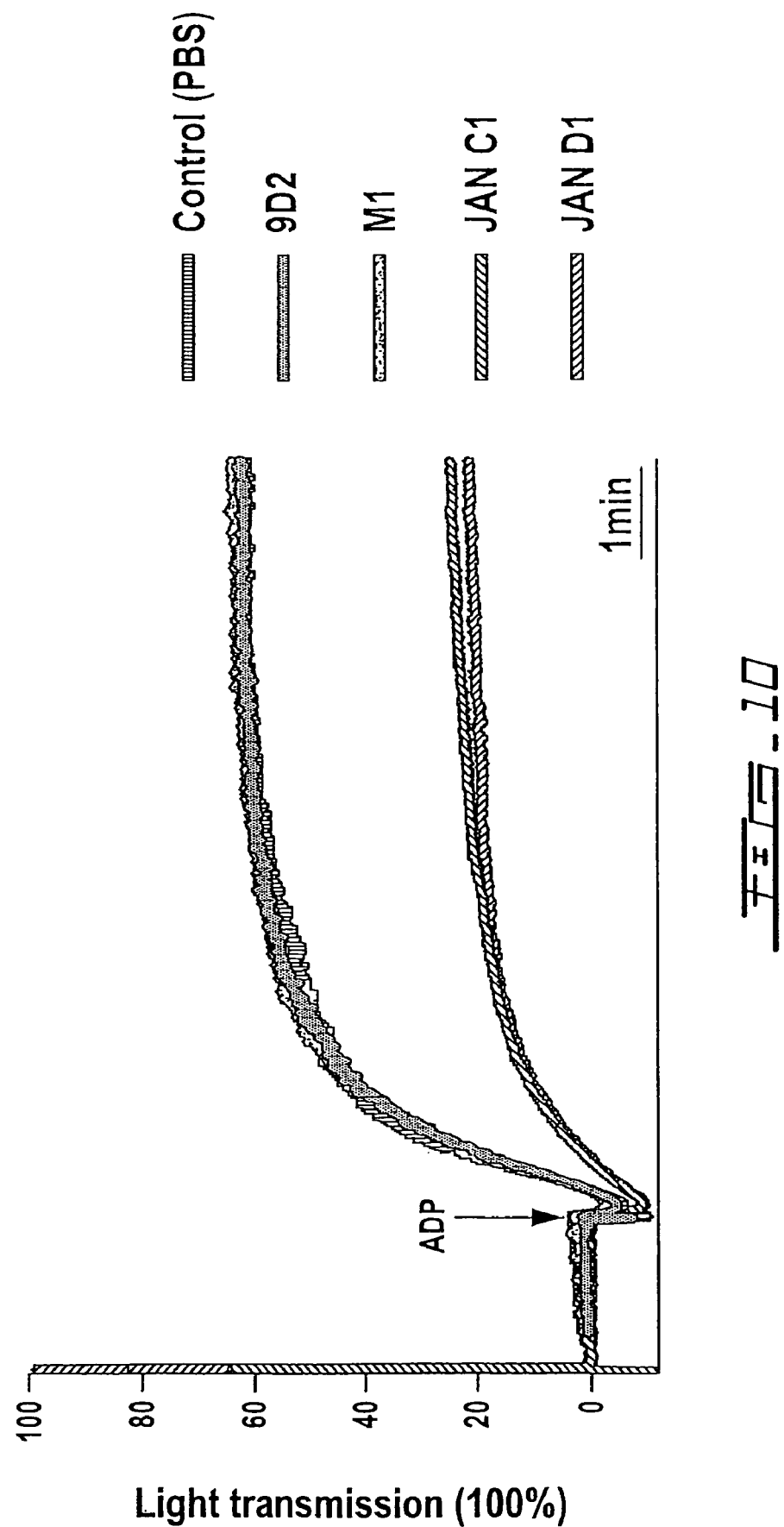
FIG. 10 is a graphical representation of the results of human platelet aggregation studies in the presence and absence of anti-mouse $\beta_3$ integrin mAbs 9D2, M1, JAN C1 and JAN D1. Human platelets were incubated with PBS (control, black), or mouse anti-mouse $\beta_3$ integrin mAbs (9D2, M1, JAN C1 or JAN D1) (40 μg/mL), which recognize human platelets, then stimulated with ADP (20 μM). Platelet aggregation (light transmission) was monitored over 12 min. JAN C1 and JAN D1 significantly inhibited human platelet aggregation.
Figure 11:
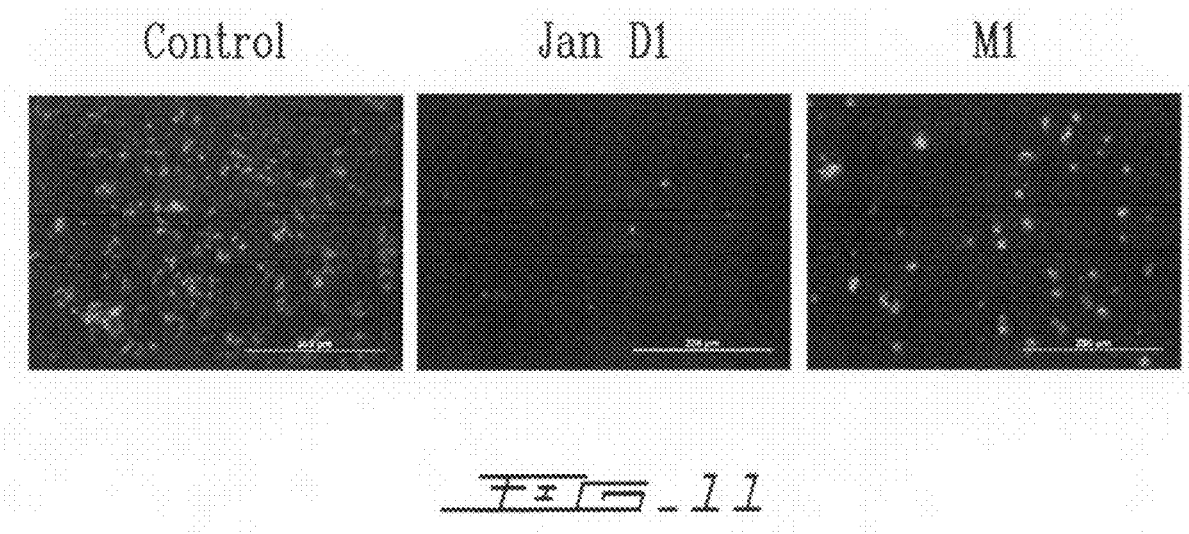
FIG. 11 shows fluorescence microscopy images illustrating human platelet deposition and adhesion on collagen surfaces in flow states. Fluorescently labeled human whole blood anti-coagulated with heparin (250 IU/mL) was incubated with PBS (control, A), JAN D1 (B) or M1 (C) at concentration of 40 μg/mL for 30 min. Blood was then perfused over a collagen coated surface at shear rate of 500 s$^{-1}$. JAN D1 and M1 significantly inhibited human platelet deposition and adhesion on collagen under these flow conditions.
Figure 17:
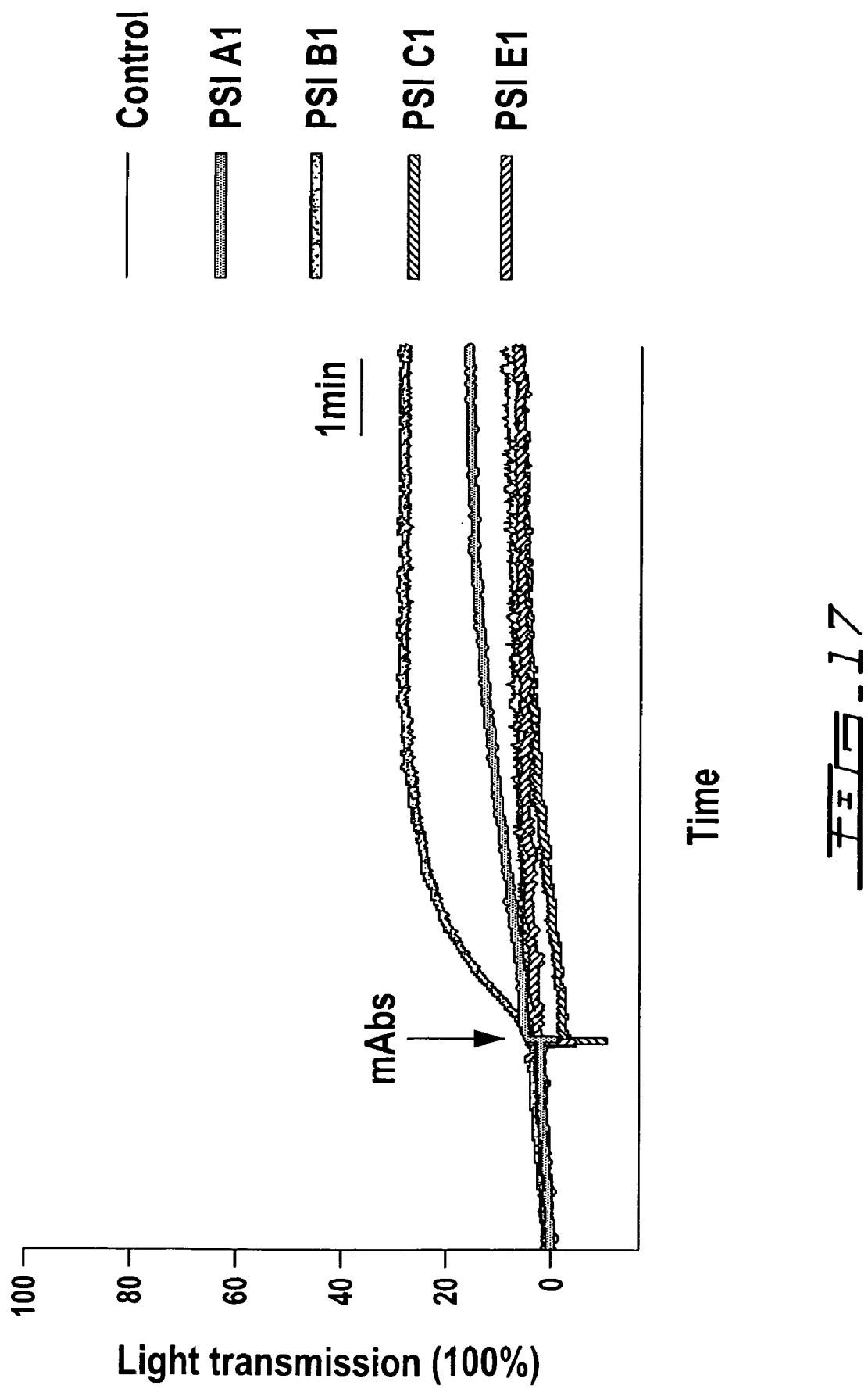
FIG. 17 shows standard aggregometry traces of human platelets stimulated with PBS (control, black), PSI A1, PSI B1, PSI C1 or PSI E1 (80 μg/ml). Platelet aggregation (light transmission) was monitored over 12 min. PSI B1 enhanced human platelet aggregation.

Of the mAbs tested, eleven mAbs (9D2, M1, JAN A1, JAN B1, JAN C1, JAN D1, DEC A1, PSI A1, PSI B1, PSI C1, PSI E1) have been shown to inhibit aggregation of mouse platelets, while JAN C1, JAN D1, PSI A1, PSI B1, PSI C1, and PSI E1 are shown to inhibit aggregation of human platelets (FIGS. 9, 10 and 17 respectively). Further, representative mAbs JAN D1 and M1 have been shown to significantly inhibit human platelet deposition and adhesion on collagen in flow states (FIGS. 11 and 12), and have been demonstrated herein to reduce thrombus formation in mice (FIG. 13).

Figure 18:
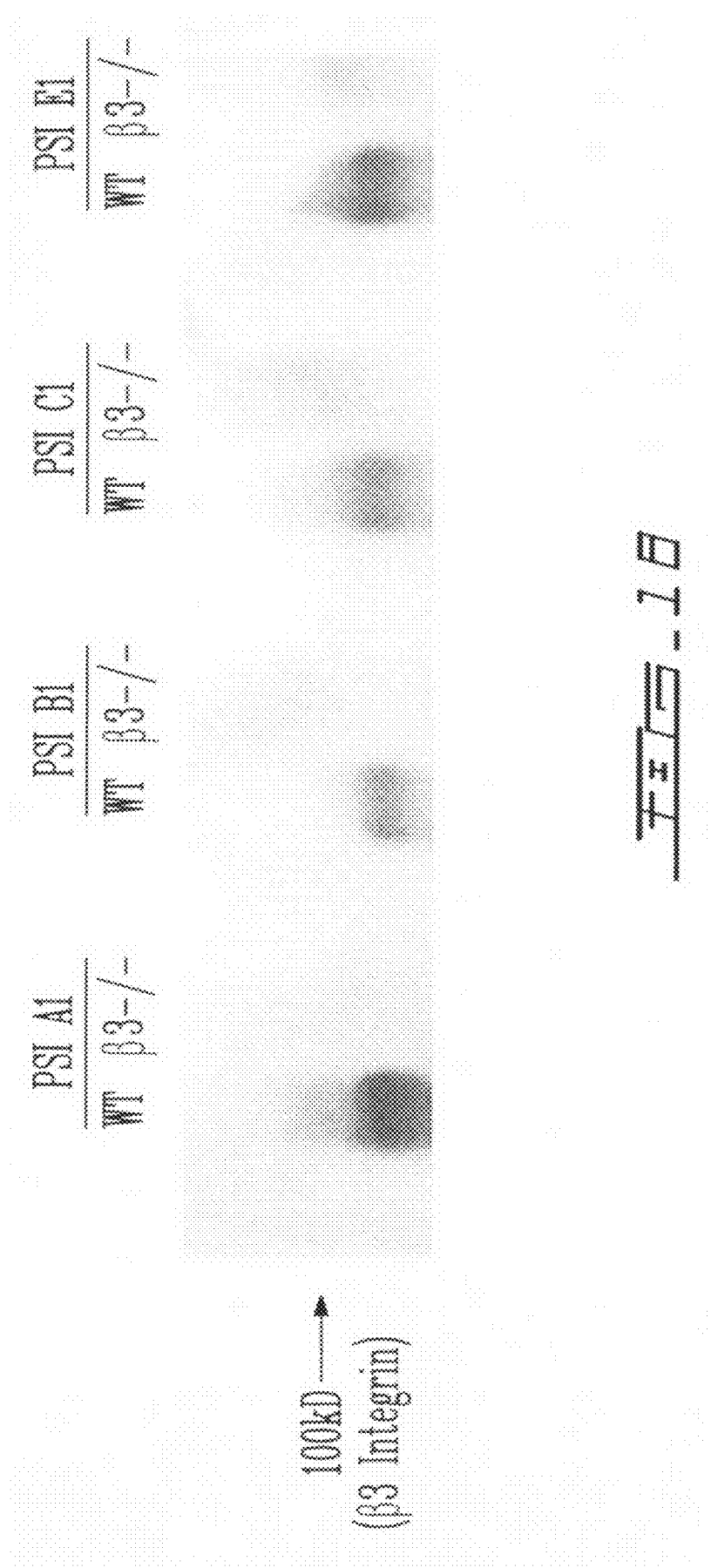
FIG. 18 shows the results of Western blot analysis of platelet lysate with monoclonal mouse anti-mouse PSI domain antibodies. Briefly, lysate from 10$^8$ WT platelets were run in each lane of a non-reducing 7% SDS-PAGE gel. After transfer to PVDF membrane, the membrane was immunoblotted with mouse anti-mouse PSI domain antibodies PSI A1, PSI B1, PSI C1 or PSI E1. Immunoreactive bands were developed by reaction with BCIP/NBT substrate. The monoclonal anti-β3 PSI domain antibodies recognize a linear epitope.
Figure 19:
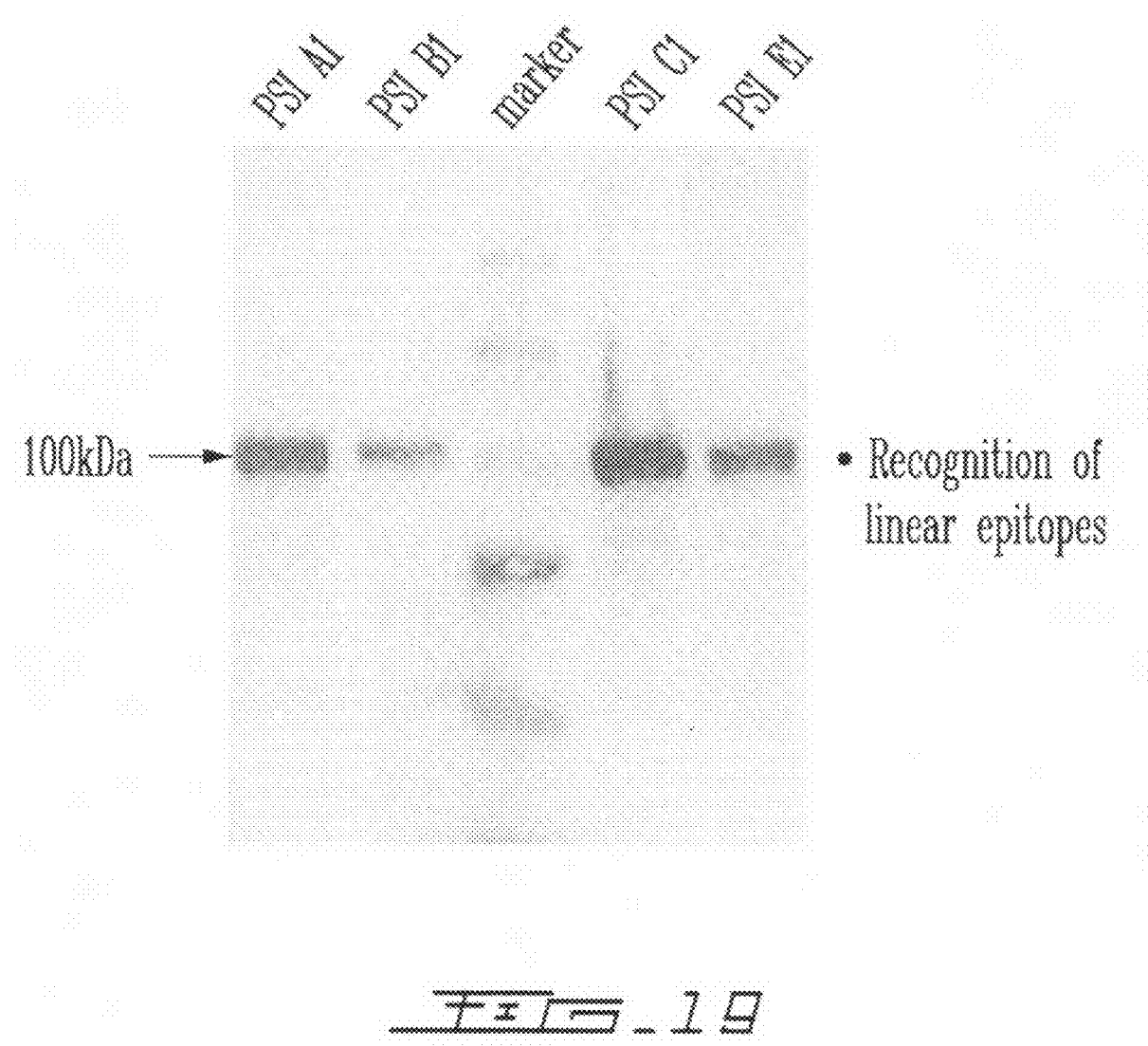
FIG. 19 shows the results of Western blot analysis of human platelet lysate with monoclonal mouse anti-mouse PSI domain antibodies. Briefly, lysate from 10$^8$ WT platelets were run in each lane of a reducing 7% SDS-PAGE gel. After transfer to PVDF membrane, the membrane was immunoblotted with mouse anti-mouse PSI domain antibodies PSI A1, PSI B1, PSI C1 or PSI E1. Immunoreactive bands were developed by reaction with BCIP/NBT substrate. All anti-β3 PSI domain antibodies recognize a linear epitope in human platelets.

Interestingly, although PSI B1 inhibits both ADP-induced mouse and human platelet aggregation in platelet rich plasma, this mAb itself can partially induce human platelet aggregation without any agonist treatment (FIG. 18), suggesting PSI B1 may initiate the "swinging out" of the leg of the β subunit but fix the integrin in partially activated conformation and prevent its further activation.

Figure 14:
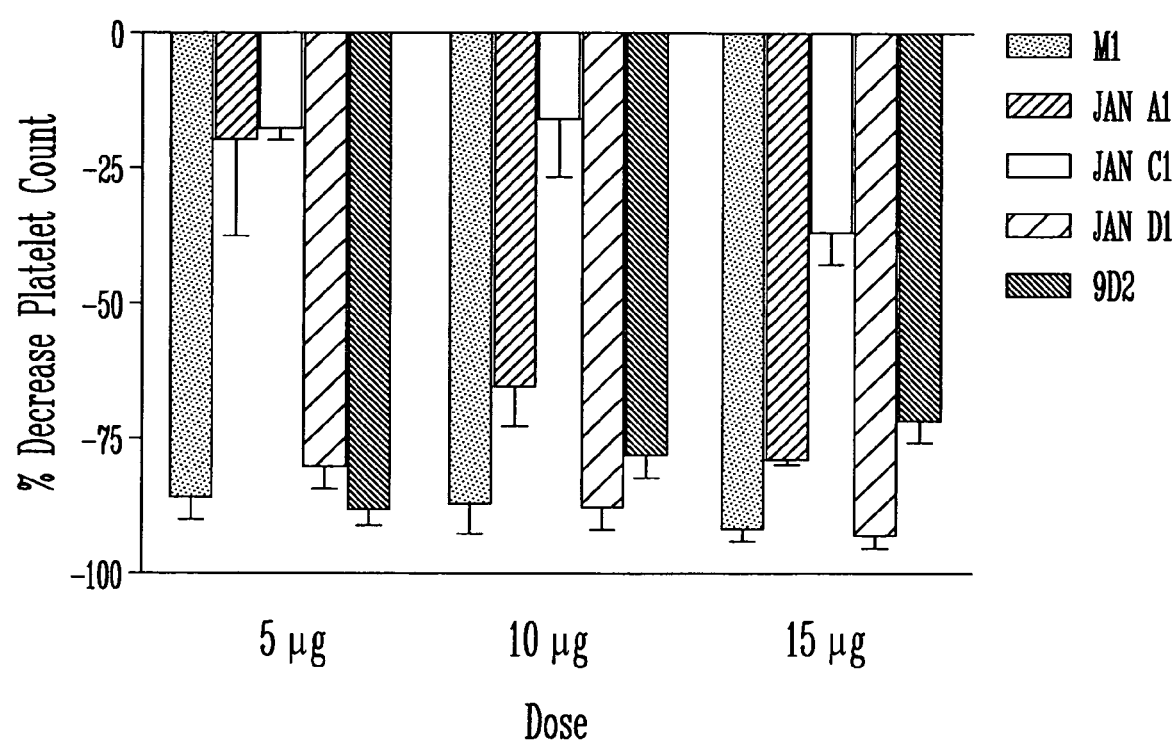
FIG. 14 is a graphical representation of the % decrease in platelet count in BALB/c mice upon administering anti-mouse β$_3$ integrin mAbs M1, JAN A1, JAN C1, JAN D1 and 9D2 to induce thrombocytopenia. BALB/c mice (6-8 weeks of age) platelets were enumerated on day 1 (basal count, 100%), and thrombocytopenia was induced by i.v. injection of one of three doses of the monoclonal antibodies: 5 μg, 10 μg, 15 μg per mouse (n=3). Platelets were enumerated 24 hours after antibody injection (day 2), and thrombocytopenia induction is represented as the percent decrease in platelet count 24 hours after antibody injection.

M1, 9D2, JAN A1, JAN C1 and JAN D1 have further been demonstrated to induce thrombocytopenia in mice (FIG. 14). Accordingly, 9D2, M1, and the anti-PSI domain mAbs can be used for murine models of antithrombotic therapy, whereas humanized forms of JAN C1, JAN D1, M1, and the anti-PSI domain mAbs have potential to be used for human antithrombotic therapy, for instance upon replacement of their constant regions with human immunoglobulin.

As suggested above, it is also possible that some antibodies binding to certain regions (epitopes) of PSI domain may fix the structure of PSI domain and prevent the process of "swinging out", therefore indirectly inhibiting integrin-ligand interaction. This possibility has not been studied before, but has been observed by the present inventors with the mAbs to PSI domain described herein. These indirect inhibitors differ from other β3 integrin antagonists such as clinical drugs REOPRO™ (abciximab), AGGRASTAT™ (tibrofan), and INTEGRELIN™ (eptifibatide) that directly interfere with integrin-ligand interaction. Since they bind the regulatory region (PSI domain), it is proposed that they will have reduced side-effect of bleeding disorders than current clinical drugs such as REOPRO™ (abciximab). These anti-PSI mAbs may further inhibit platelet recruitment for thrombus growth (i.e., with anti-thrombotic potential), but only mildly affect platelet adhesion and aggregation at the direct site of vascular injury (i.e., they do not significantly affect hemostasis).

In addition to its anti-thrombotic effect, PSI B1 may be able to induce ligand binding as it may induce "swinging out" of the leg of the β subunit. This unique mAb (dual role) may be used as platelet activators with therapeutic potential to stop bleeding.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently disclosed subject matter.

Example 1

Generation of Monoclonal Antibodies Using β3 Integrin Gene Knockout Mice

Monoclonal antibodies were produced in accordance with the scheme illustrated in FIG. 2. In brief, BALB/C wild type mice were bled under ether anesthesia from retro-orbital plexus. Blood was collected in a tube containing 1% EDTA PBS, then was centrifuged at 1000 rpm for 10 minutes at room temperature. Platelet Rich Plasma was collected and further centrifuged at 2300 rpm for 10 minutes. Platelets were washed twice with PBS. $\beta_3$ integrin deficient BALB/C mice, 6 to 8 weeks of age, were transfused with $1 \times 10^8$ washed BALB/c wild-type mouse platelets for 6 times, once a week. Transfused $\beta_3$ integrin deficient BALB/C mice spleen cells were fused with mouse myeloma cells (Ag 8.653), and hybridomas were selected in HAT medium. Hybridomas secreting mAbs directed against $\beta_3$ integrin were identified by flow cytometry, and subcloned twice before large-scale production. Monoclonal antibodies were produced and purified according to standard methods.

Briefly, antibody positive hybridoma cells were transferred into commercial HyQ ADCF-MAb™ sera-free medium (Hy-Clone, Logan, Utah, USA) in cell culture flasks (500 ml). Hybridoma cells were allowed to grow until they die, then the medium was collected. The medium was centrifuged at 5000 rpm, for 20 minutes at room temperature to remove the cells. The supernatant was collected, and diluted 1:1 with commercial ImmunoPure IgG™ Binding Buffer (Pierce Biotechnology, Inc. Rockford, Ill., USA), then passed through a Protein G coupled sepharose column. Subsequently, the column was washed with binding buffer, and antibody was eluted after adding commercial ImmunoPure IgG™ Elution Buffer (Pierce Biotechnology, Inc.). The fractions of antibodies in elution buffer were collected in individual Eppendorf™ (microfuge) tubes. The optical density (OD) of each fraction was measured at $A_{280}$ (to detect proteins), and the high concentration fractions were dialysed using a dialysis membrane in phosphate buffered saline.

Example 2

Binding of mAbs to Mouse Platelets, Human Platelets, and $\beta_3$ Integrin Deficient ($\beta_3^{-/-}$) Mouse Platelets Materials: BALB/c wild-type mice; β3 integrin deficient BALB/C mice; Mouse myeloma cells (Ag 8.653); FITC-goat anti-mouse IgG (sigma); FACScan (Becton Dickinson).

Figure 3:
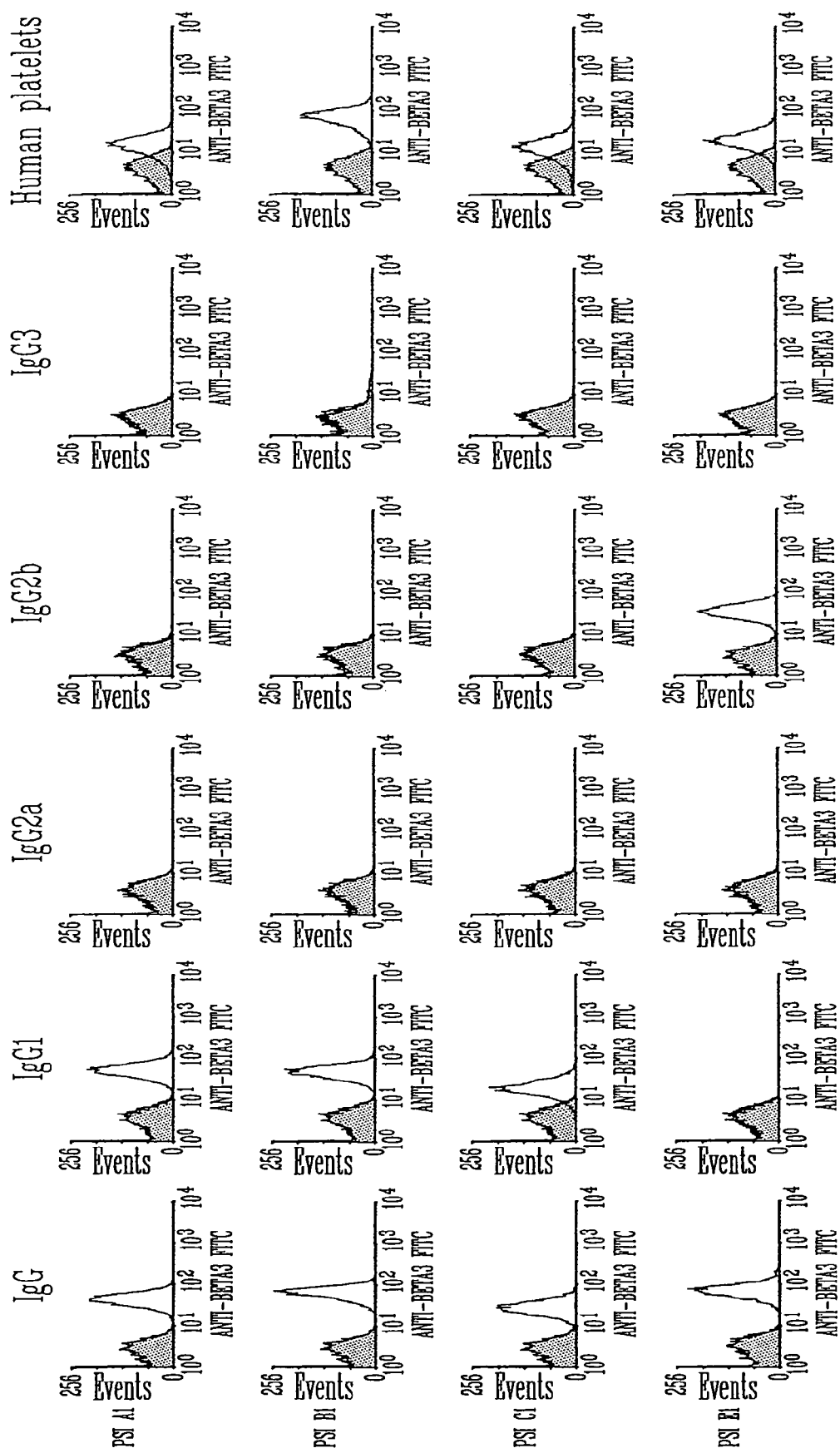
FIG. 3 is a graphical (histogram) representation of the results of analysis by flow cytometry of anti-mouse PSI domain of $\beta_3$ integrin mAbs (PSI A1, B1, C1, E1) binding to wild type mouse platelets and healthy human platelets. Washed wild-type (WT) platelets were incubated with each mAb (black line) or antibody-negative fusions (filled peak) then incubated with FITC-conjugated anti-mouse-IgG, -IgG1, -IgG2a, -IgG2b and -IgG3 and analyzed. All these mAbs can recognize mouse and human $\beta_3$ integrin PSI domain. Results of isotype analysis are shown.

Method: $1\times10^6$ washed wild-type platelets (FIG. 4), human platelets (FIG. 5), or $\beta_3$ integrin deficient ($\beta_3^{-/-}$) mouse platelets (FIG. 7) were incubated with PBS (control), or mAb for 1 hour, then stained with FITC-labeled goat anti-mouse IgG (FIGS. 4, 5, 7) for 45 min. For isotype analysis (Table 1, FIG. 3), $1\times10^6$ washed wild-type platelets were incubated with mAb or antibody-negative fusions for 1 hour, then stained with FITC-labeled goat anti-mouse IgG, IgG1, IgG2a, IgG2b, IgG3 for 45 min. Samples were analyzed by flow cytometry.

Example 3

Platelet Aggregation Analysis

Figure 15A:
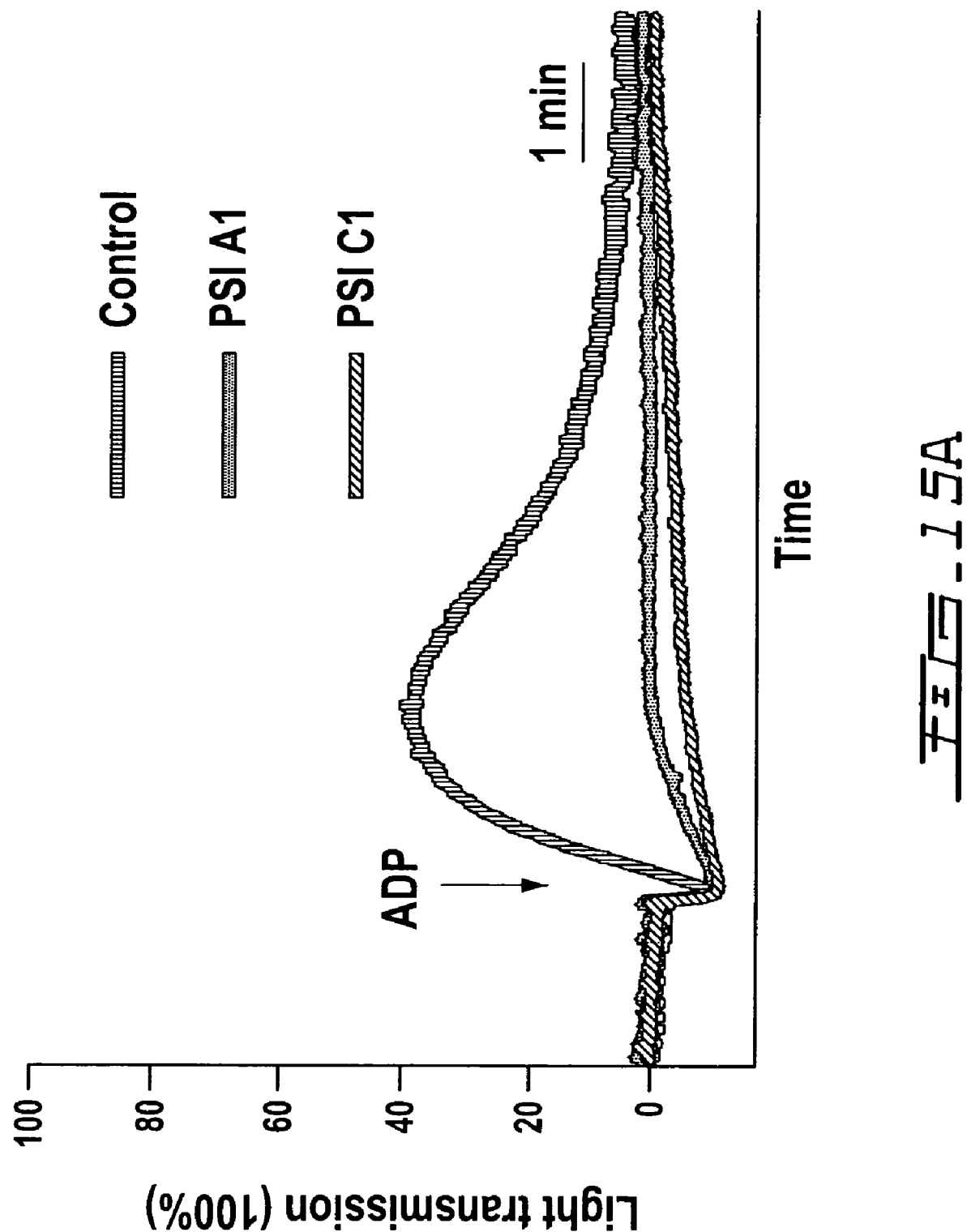
Figure 16:
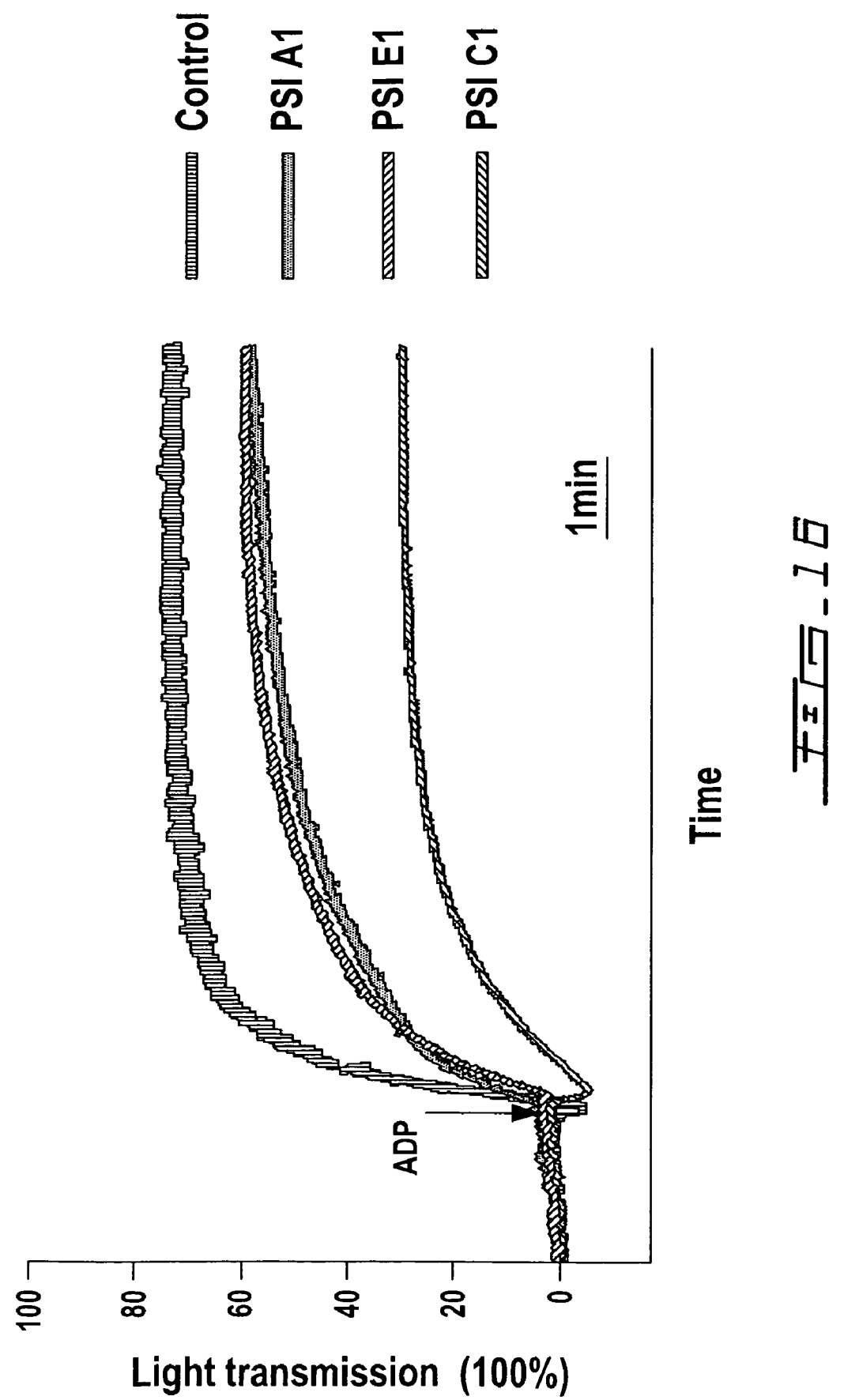
FIG. 16 shows standard aggregometry traces of human platelets incubated with PBS (black), anti-PSI domain mAbs, PSI A1, PSI C1 or PSI E1 (80 μg/ml), then stimulated with ADP (20 μM). Platelet aggregation (light transmission) was monitored over 12 min. PSI C1 significantly inhibited human platelet aggregation. PSI A1 and PSI E1 inhibited human platelet aggregation partially.

Mouse platelets (FIGS. 9, 15) or human platelets (FIGS. 10, 16, 17) were incubated with PBS (control), or mouse anti-mouse $\beta_3$ integrin mAbs, 9D2, M1, JAN C1 or JAN D1, then stimulated with ADP (20 μM). Platelet aggregation (light transmission) was monitored over 12 min. 9D2 and M1 significantly inhibited mouse platelet aggregation, while JAN C1 and JAN D1 significantly inhibited human platelet aggregation.

Example 4

Analysis of Human Platelet Adhesion Ex Vivo

Fluorescently labeled, heparin (250 IU/mL) anti-coagulated human whole blood incubated with PBS (control; FIG. 11A), JAN D1 (FIG. 11B) or M1 (FIG. 11C) for 30 min was perfused over a collagen coated surface at a shear rate of 500 $s^{-1}$. By measuring surface coverage in the flow state (FIG. 12), whole human blood treated with JAN D1 and M1 significantly decreased the percentage of platelet surface coverage (**P<0.004, *P<0.05). Adhesion of fluorescently labeled platelets was monitored and quantitated using intravital microscopy as previously described (J Thromb Haemost. October 2006; 4(10):2230-7; J Thromb Haemost. May 2005; 3(5):875-83).

Example 5

Inhibition of Mouse Thrombus Formation

In wild type (wt) C57/BL6 control mice (FIG. 13A), single fluorescent platelets started to adhere at the site of vessel injury several minutes after $FeCl_3$ injury. Visible thrombi were formed and injured arteriole was occluded at 18 min. In JAN D1 (FIG. 13B) and M1 (FIG. 13C) treated mice, single platelets adhered to the injured site and formed some small aggregates but significantly delayed and failed to form occlusive thrombi (n=2). Time after $FeCl_3$ injury is indicated in the corners of the respective images (min). Images were captured using intravital microscopy as described previously (J Thromb Haemost. October 2006; 4(10):2230-7; J Thromb Haemost. May 2005; 3(5):875-83; Proc Natl Acad Sci USA. Mar. 4, 2003; 100(5):2415-9; J Clin Invest. August 2000; 106(3):385-92; Blood. Nov. 15, 2003; 102(10):3609-14).

Example 6

Induction of Thrombocytopenia by M1, 9D2, JAN A1, JAN C1 and JAN D1

BALB/c mice (6-8 weeks of age) platelets were enumerated on day 1 (basal count, 100%). Thrombocytopenia was induced by i.v. injection of one of three doses of anti-monoclonal antibodies M1, JAN A1, JAN C1, JAN D1, and 9D2: 5 μg, 10 μg, 15 μg per mouse (n=3). Platelets were again enumerated 24 hours after antibody injection (day 2). Thrombocytopenia induction is represented in FIG. 14 as the percent decrease in platelet count 24 hours after antibody injection. The method to induce thrombocytopenia has been described in Blood. Aug. 1, 2006; 108(3):943-946.

REFERENCES

All references cited in the instant disclosure, including but not limited to all patents, patent applications and publications thereof, scientific journal articles, and database entries (e.g., GENBANK® database entries and all annotations available therein) are incorporated herein by reference in their entireties to the extent that they supplement, explain, provide a background for, or teach methodology, techniques, and/or compositions employed herein.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A hybridoma cell line having International Depositary Authority of Canada (IDAC) Accession No. selected from 230507-03, 230507-01, 230507-02, 230507-08, 190607-03, 190607-05, 190607-01, 190607-02, 230507-04, 230507-05, 230507-06 and 230507-07.

2. An isolated and purified antibody produced by a hybridoma cell of claim 1, an antibody having the antigen binding fragment thereof, or a fragment of the antibody produced by the hybridoma cell line which binds platelet integrin $\beta_3$.

3. The isolated and purified antibody of claim 2, wherein the antibody or antigen binding fragment is humanized.

4. A monoclonal antibody produced by a hybridoma cell line of claim 1.

5. A pharmaceutical composition comprising the isolated and purified antibody, antibody fragment, or monoclonal antibody defined in any one of claims 2 to 4, and a pharmaceutical acceptable carrier.

6. The pharmaceutical composition according to claim 5 for inhibiting platelet aggregation.

7. The pharmaceutical composition according to claim 5 for antithrombotic treatment.

8. The pharmaceutical composition according to claim 5 for platelet activation, wherein the isolated and purified antibody, antibody fragment, or monoclonal antibody is derived from the hybridoma cell line 230507-05.

9. The pharmaceutical composition according to claim 5 for inhibition of angiogenesis.

10. A solid phase having attached thereto the isolated and purified antibody, antibody fragment, or monoclonal antibody defined in any one of claims 2 to 4.

11. The solid phase according to claim 10, wherein said solid phase comprises a gel, a hydrogel, a resin, a bead, nitrocellulose, a nylon membrane, a micrometer plate, a culture flask, or a polymeric material.

12. The solid phase according to claim 10, for separation or isolation of $\beta_3$ integrin.

13. The solid phase according to claim 12, wherein said solid phase comprises a gel, a hydrogel, a resin, a bead, nitrocellulose, a nylon membrane, a micrometer plate, a culture flask, or a polymeric material.

14. A purified antibody, antibody fragment, or monoclonal antibody as defined in any one of claims 2 to 4, labelled with a detectable marker or conjugate.

15. The purified antibody, antibody fragment or monoclonal antibody according to claim 14, wherein said detectable marker is a fluorescent or radioactive marker.

16. The purified antibody, antibody fragment or monoclonal antibody according to claim 14, wherein said conjugate is biotin, or an enzyme selected from peroxidise or alkaline phosphatase.

17. A method for measuring $\beta_3$ integrin expression, said method comprising obtaining an integrin positive cell sample and measuring $\beta_3$ integrin expression with an antibody produced by a hybridoma cell line of claim 1, an antibody having the antigen binding fragment thereof, or a fragment of the antibody produced by the hybridoma cell line of claim 1, which binds platelet integrin $\beta_3$.

18. The method of claim 17, wherein the integrin positive cell sample is a sample of cellular material capable of expressing $\beta_3$ integrin.

19. The method of claim 17 or 18, wherein the cell sample is selected from platelets, macrophages, leukocytes, and new growth endothelial cells.

20. A method for measuring platelet count, said method comprising:
    (i) obtaining a platelet sample;
    (ii) contacting an antibody produced by a hybridoma cell line of claim 1, an antibody having the antigen binding fragment thereof, or a fragment of the antibody produced by the hybridoma cell line of claim 1, which binds platelet integrin $\beta_3$ so as to form a complex with the platelet; and
    (iii) measuring platelet count by detecting the complex formed in step (ii).

21. A method of antithrombotic treatment comprising administering an antibody produced by a hybridoma cell line of claim 1, an antibody having the antigen binding fragment thereof, or a fragment of the antibody produced by the hybridoma cell line of claim 1, which binds platelet integrin $\beta_3$ and acceptable carrier, to an individual in need thereof in an amount effective to treat thrombosis.

22. A method of inhibiting platelet aggregation comprising administering an antibody produced by a hybridoma cell line of claim 1, an antibody having the antigen binding fragment thereof, or a fragment of the antibody produced by the hybridoma cell line of claim 1, which binds platelet integrin $\beta_3$ and acceptable carrier, to an individual in need thereof in an amount effective to inhibit platelet aggregation.

23. A method of platelet activation comprising administering an antibody produced by a hybridoma cell line of claim 1 having International Depositary Authority of Canada Accession No. 230507-05, an antibody having the antigen binding fragment thereof, or a fragment of the antibody produced by the hybridoma cell line of claim 1 having International Depositary Authority of Canada Accession No. 230507-05, which binds platelet integrin $\beta_3$ and acceptable carrier, to an individual in need thereof in an amount effective for platelet activation.

* * * * *